United States Patent [19]

Ashton et al.

[11] Patent Number: 5,262,412
[45] Date of Patent: Nov. 16, 1993

[54] SUBSTITUTED PYRAZOLES, COMPOSITIONS AND USE

[75] Inventors: Wallace T. Ashton, Clark; Linda L. Chang, Wayne; William J. Greenlee, Teaneck; Steven M. Hutchins, Iselin, all of N.J.

[73] Assignee: Merck & Co., Inc., Rahway, N.J.

[21] Appl. No.: 28,845

[22] Filed: Mar. 10, 1993

[51] Int. Cl.$^5$ ................ A61K 31/415; C07D 231/12; C07D 413/12
[52] U.S. Cl. .................... 514/236.5; 514/341; 514/406; 544/140; 546/274; 548/365.7; 548/375.1; 548/377.1
[58] Field of Search ............ 544/140; 546/274; 548/365.7, 375.1, 377.1; 514/236.5, 341, 406

[56] References Cited

FOREIGN PATENT DOCUMENTS 446062  9/1991 European Pat. Off. .
449699 10/1991 European Pat. Off. .
91/15479 10/1991 World Int. Prop. O. .

*Primary Examiner*—Robert W. Ramsuer
*Attorney, Agent, or Firm*—Joseph F. DiPrima

[57] ABSTRACT

Substituted pyrazole compounds are angiotensin II antagonists and therefore useful in the treatment of hypertension, and related cardiovascular disorders and ocular hypertension. These compounds have the general formula I:

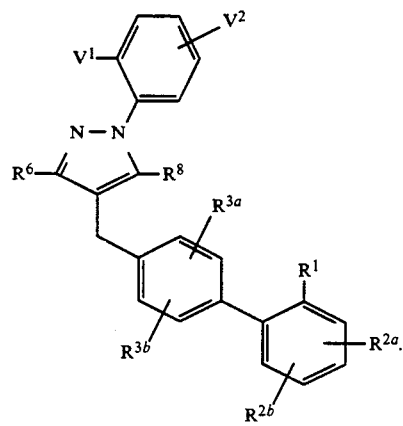

7 Claims, No Drawings

SUBSTITUTED PYRAZOLES, COMPOSITIONS AND USE

SUMMARY OF THE INVENTION

This invention relates to novel substituted pyrazole compounds and derivatives thereof which are angiotensin II antagonists useful in the treatment of hypertension and related cardiovascular disorders and in ocular hypertension.

It also relates to pharmaceutical compositions comprising one of the novel compounds as active ingredient and to methods of treating hypertension, including ocular hypertension, and related cardiovascular disorders.

It further relates to novel processes for making the novel compounds.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (A II) is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption.

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu, et al. [*Eur. J. Pharm. Exp. Therap,* 157, 13-21 (1988)] and by P. C. Wong, et al. [*J. Pharm. Exp. Therap,* 247, 1-7 (1988)]. All of the U.S. Patents, European Patent Applications 028,834 and 253,310 and the two articles disclose substituted imidazole compounds which are generally bonded through a lower alkyl bridge to a substituted phenyl. Non-peptide A-II antagonists with a pyrazole heterocycle are described in published Patent applications WO 91/15479 (Merck); EP 446,062 (Glaxo); and EP 449,699 (Laboratories UPSA).

DETAILED DESCRIPTION OF THE INVENTION

The novel compounds of this invention have the general formula I:

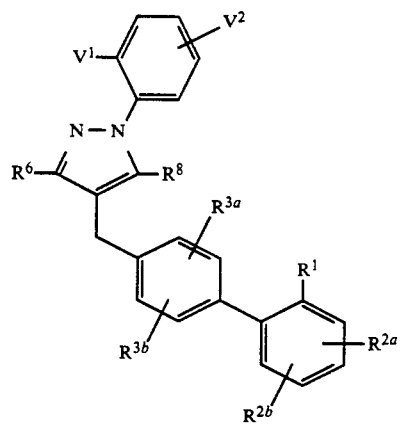

or a pharmaceutically acceptable salt thereof wherein:
$R^1$ is $-SO_2NHCOR^{23}$ or $-SO_2NHCO_2R^{24}$;
$R^{2a}$ and $R^{2b}$ are independently: H, F, Cl, $CF_3$ or $C_1-C_4$-alkyl;
$R^{3a}$ is H or F;
$R^{3b}$ is H, F, Cl, $CF_3$ or $C_1-C_4$-alkyl;
$R^6$ is $C_1-C_6$-alkyl;
$R^8$ is H, F, Cl, Br, I, $-OH$, $-O(C_1-C_4$-alkyl), $-S(O)_p(-C_1-C_4$-alkyl), $-NH_2$, $-NH(C_1-C_4$-alkyl), $-N(-C_1-C_4$-alkyl$)_2$, $-CN$, $-CO_2H$, $-CO_2(C_1-C_4$-alkyl), $-CONH_2$, $CONH(C_1-C_4$-alkyl) or $-CON-(C_1-C_4$-alkyl$)_2$;
$V^1$ is $CH_3$, $CF_3$, Cl, Br, I, F, $OCH_3$, $SCH_3$, $-NO_2$ or $-CN$;
$V^2$ is a group at the 4- or 5-position selected from:
 (a) $-NR^{21}COR^{22}$,
 (b) $-NR^{21}CO_2R^{22}$,
 (c) $-NR^{21}CONR^{21}R^{22}$,

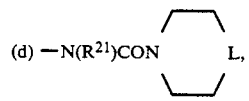

(e) $-CONR^{21}R^{22}$,

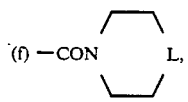

(g) $-COR^{22}$,
 (h) $-S(O)_pR^{22}$,
 (i) $-SO_2NR^{21}R^{22}$,

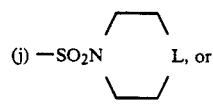

(k) $-NR^{21}SO_2R^{22}$,
wherein L is a single bond, $CH_2$, O, $S(O)_p$, or $NR^9$, and p is 0 to 2;
$R^{21}$ is:
 (a) H or
 (b) straight chain or branched $C_1-C_6$-alkyl, $C_3-C_6$-alkenyl, or $C_3-C_6$-alkynyl, each of which is unsubstituted or substituted with one or more substituents selected from the group consisting of aryl, heteroaryl, $C_3$–$C_6$-cycloalkyl, Cl, Br, I, F, —OH, —O($C_1$–$C_4$-alkyl), —S($C_1$–$C_4$-alkyl), —O-phenyl or —S-phenyl;

$R^{22}$ is:
(a) straight chain or branched $C_1$–$C_6$-alkyl, $C_2$–$C_6$-alkenyl, or $C_2$–$C_6$-alkynyl, each of which is unsubstituted or substituted with one or more substituents selected from the group consisting of aryl, heteroaryl, $C_3$–$C_6$-cycloalkyl, Cl, Br, I, F, —OH, —O($C_1$–$C_4$-alkyl), —S($C_1$–$C_4$-alkyl), —O-phenyl or —S-phenyl,
(b) $C_3$–$C_7$-cycloalkyl unsubstituted or substituted with one or more substituents selected from the group consisting of $C_1$–$C_4$-alkyl, Cl, Br, I, F or phenyl,
(c) aryl, or
(d) heteroaryl;

$R^{23}$ is:
(a) aryl,
(b) heteroaryl,
(c) straight chain or branched $C_1$–$C_6$-alkyl, $C_3$–$C_6$-alkenyl, or $C_3$–$C_6$-alkynyl, each of which is unsubstituted or substituted with one or more substituents selected from the group consisting of aryl, heteroaryl, $C_3$–$C_6$-cycloalkyl, Cl, Br, I, F, —OH, —O($C_1$–$C_4$-alkyl), —S($C_1$–$C_4$-alkyl), —O-phenyl or —S-phenyl,
(d) $C_3$–$C_7$-cycloalkyl unsubstituted or substituted with one or more substituents selected from the group consisting of $C_1$–$C_4$-alkyl, Cl, Br, I, F or phenyl,
(e) $C_7$–$C_{10}$-bi- or tricycloalkyl, or
(f) saturated 5- or 6-membered heterocyclyl linked through a carbon atom and containing one or two heteroatoms selected from oxygen or sulfur;

$R^{24}$ is:
(a) straight chain or branched $C_1$–$C_6$-alkyl, $C_3$–$C_6$-alkenyl, or $C_3$–$C_6$-alkynyl, each of which is unsubstituted or substituted with one or more substituents selected from the group consisting of aryl, $C_3$–$C_6$-cycloalkyl, Cl, Br, I, F, —O($C_1$–$C_4$-alkyl), —S($C_1$–$C_4$-alkyl), —O-phenyl or —S-phenyl,
(b) $C_3$–$C_7$-cycloalkyl unsubstituted or substituted with one or more substituents selected from the group consisting of $C_1$–$C_4$-alkyl, Cl, Br, I, F or phenyl, or
(c) aryl.

The terms "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The terms "halo" and "halogen" mean Cl, Br, I or F.

The term "aryl" is defined as phenyl or naphthyl, unsubstituted or substituted with one, two, or three substituents selected from the group consisting of $C_1$–$C_4$-alkyl, $C_1$–$C_4$-alkoxy, Cl, Br, F, I, $CF_3$, $C_1$–$C_4$-alkyl-S(O)$_p$—, $CF_3SO_2$—, and —CN.

The term "heteroaryl" is defined as a 5- or 6-membered aromatic ring consisting of carbon and 1 or 2 heteroatoms selected from the group consisting of N, O, and S, such as pyridine, pyrimidine, pyrazine, triazine, furan, thiophene, oxazole, thiazole, imidazole, or the like, which can be fused to a benzo group and can be unsubstituted or substituted wherein the substituents are selected from the group consisting of $C_1$–$C_4$-alkyl, $C_1$–$C_4$-alkoxy, —$CF_3$, Cl, Br, F and I.

The term "saturated 5- or 6-membered saturated heterocyclyl includes piperazinyl, morpholinyl, tetrahydrofuryl, tetrahydrothienyl, tetrahydropyranyl, tetrahydrothiopyranyl, dioxolanyl, dithiolanyl, dithianyl and the like.

The term "$C_7$–$C_{10}$-bi- or tricycloalkyl" includes such as norbornan-2-yl, adamantan-1-yl or noradamantan-3-yl, either unsubstituted or substituted with $C_1$–$C_2$-alkyl.

One embodiment of the novel compounds is that wherein;

$R^{2a}$ is H or F;
$R^{2b}$ is H, F or $C_1$–$C_4$-alkyl;
$R^{3b}$ is H, F or Cl;
$R^6$ is n-propyl or n-butyl;
$R^8$ is —CN, —$CO_2H$, —$CO_2(C_1$–$C_4$-alkyl), —$CONH_2$, —$CONH(C_1$–$C_4$-alkyl) or —$CON(C_1$–$C_4$-alkyl)$_2$;
$R^{21}$ is H;
$R^{23}$ is:
(a) phenyl, unsubstituted or substituted with one or two substituents chosen from Cl, Br, F, I, methyl or trifluoromethyl, at least one of which occupies an ortho-position;
(b) heteroaryl, selected from furan-2-yl, thiophen-2-yl, benzo[b]furan-2-yl, benzo[b]thiophen-2-yl, furan-3-yl, thiophen-3-yl, and oxazol-5-yl, unsubstituted or substituted with one or two substituents chosen from Cl, Br, F, I, methyl or trifluoromethyl, wherein at least one of the substituents is located adjacent to the carbonyl substituent and/or to a ring heteroatom;
(c) branched $C_3$–$C_6$-alkyl;
(d) $C_3$–$C_7$-cycloalkyl, unsubstituted or substituted at the 1- and/or 2-position with one or two substituents chosen from Cl, Br, F, I, methyl or ethyl;
(e) $C_7$–$C_{10}$-bi- or tricycloalkyl; or
(f) saturated 5- or 6-membered heterocyclyl linked through a carbon atom and containing one or two heteroatoms selected from oxygen and sulfur;

$R^{24}$ is straight chain or branched $C_1$–$C_6$-alkyl, $C_3$–$C_6$-alkenyl, or $C_3$–$C_6$-alkynyl, each of which is unsubstituted or substituted with aryl or $C_3$–$C_6$-cycloalkyl;

$V^1$ is $CF_3$, Cl, Br, I, or F;
$V^2$ is a group at the 5-position selected from:
(a) —$NR^{21}COR^{22}$;
(b) —$NR^{21}CO_2R^{22}$;
(c) —$NR^{21}CONR^{21}R^{22}$;

(d) 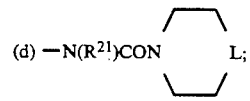

(e) —$CONR^{21}R^{22}$;

(f) 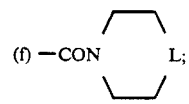

(g) —$COR^{22}$; or
(h) —$S(O)_pR^{22}$.

DISCUSSION OF CHEMISTRY AND REACTION SCHEMES

The compounds of Formula I can be prepared by a variety of methods typified by those described below. General synthetic methods for substituted 1H-pyrazoles are discussed in review articles or books such as L. C. Behr, R. Fusco, and C. H. Jarboe, "Pyrazoles, Pyrazolines, Pyrazolidines, Indazoles and Condensed Rings" (R. H. Wiley, ed.), Interscience, New York, 1967.

Although the Reaction Schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions (including reagents, solvent, temperature, and reaction time) should be chosen so that they are consistent with the nature of the functionality present in the molecule.

The Reaction Schemes below have been generalized for simplicity. It is to be understood that where the substituent present at $C^4$ of the pyrazole (or precursors thereof) is indicated as "$ArCH_2$" this group represents any substituted arylmethyl moiety consistent with the definition of the $C^4$ substituent in Formula I or which may be transformed to such a grouping either before or after assembly of the pyrazole ring system. Such transformations may involve protection and/or deprotection, or other modifications. Similarly, "Ar" at $N^1$ of the pyrazole represents any aryl group consistent with the definition of Formula I at this position or which can be transformed to such a grouping. Other generalized substituents such as R, R', and R" represent functionalized alkyl, aryl, heteroaryl, aralkyl, and the like, consistent with the definition of Formula I or its precursors. The group "X" is a leaving group or counterion such as chloro, bromo, iodo, methanesulfonate, or p-toluenesulfonate, as in an alkylating agent RX or a Grignard reagent RMgX.

Abbreviations used in the reaction schemes, chemistry discussion, and examples are listed in Table 1.

TABLE 1

| Reagents | |
|---|---|
| TFA | trifluoroacetic acid |
| CDI | 1,1'-carbonyldiimidazole |
| DBU | 1,8-diazabicyclo[5.4.0]undec-7-ene |
| NBS | N-bromosuccinimide |
| NCS | N-chlorosuccinimide |
| AIBN | 2,2'-azobis(isobutyronitrile) |
| BOP reagent | benzotriazol-1-yloxytris(dimethylamino)phosphonium hexafluorophosphate |
| PPE | polyphosphate ester |
| Solvents | |
| EtOH | ethanol |
| DMF | dimethylformamide |
| AcOH | acetic acid |
| MeCN | acetonitrile |
| EtOAc | ethyl acetate |
| MeOH | methanol |
| THF | tetrahydrofuran |
| DMSO | dimethyl sulfoxide |
| Other | |
| Me | methyl |
| Et | ethyl |
| iPr | isopropyl |
| Bu | n-butyl |
| t-Bu (or Bu-t) | t-butyl |
| iAm | isoamyl |
| Ph | phenyl |
| Im | imidazol-1-yl |
| mol. | molecular |
| aq. | aqueous |
| cat. | catalytic |
| R, R', etc. | any group (e.g., alkyl or aryl) compatible with the definitions of Formula I |
| Ar, Ar' | any aryl group compatible with the definitions of Formula I (or precursors thereof) |
| X | a halogen or other leaving group such as p-toluenesulfonate |
| FAB | fast atom bombardment |
| EI | electron impact |
| atm. | atmospheres (of pressure) |

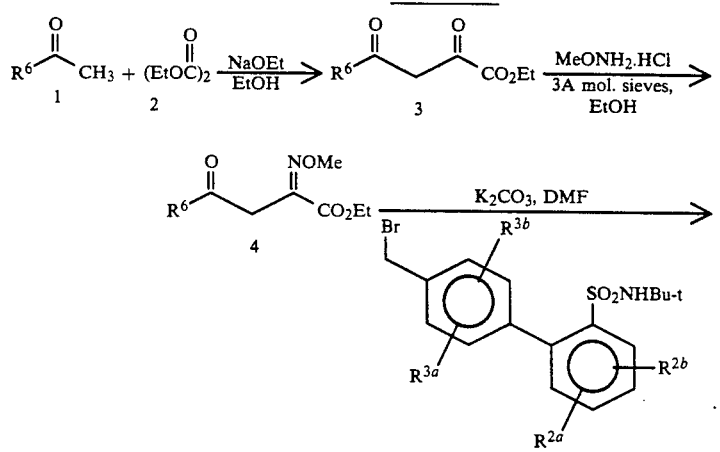

SCHEME 1

-continued
SCHEME 1
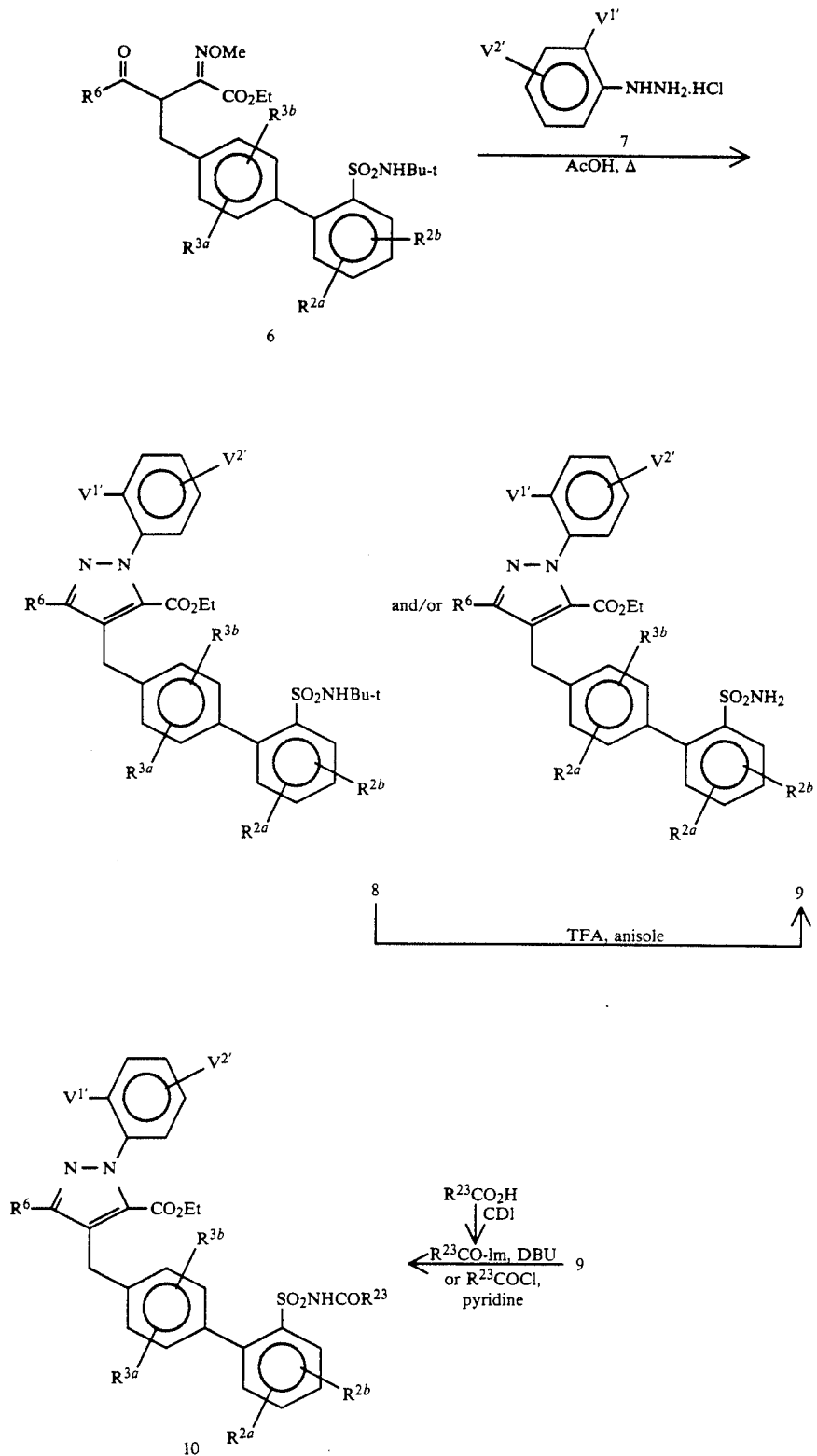

SCHEME 1

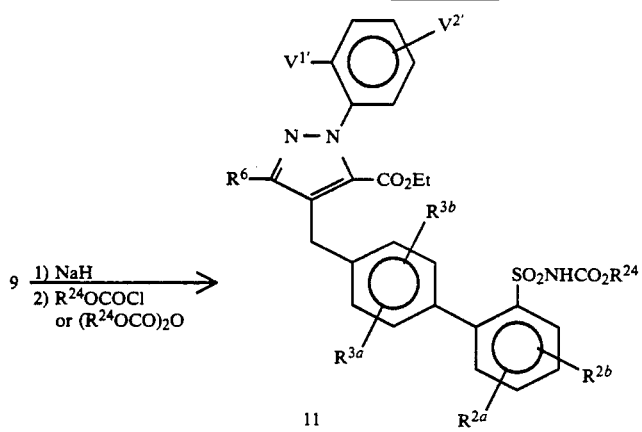

where $V^{1'}$ and $V^{2'}$ are $V^1$ and $V^2$, respectively, or precursors thereof.

A useful generalized pathway for the synthesis of compounds of Formula I wherein $R^8$ is a carboxylic acid ester is illustrated in Scheme 1. Reaction of the appropriate methyl ketone 1 with diethyl oxalate 2 in the presence of sodium ethoxide yields the 2,4-diketo ester 3 [D. Libermann, N. Rist, F. Grumbach, S. Cals, M. Moyeux, and A. Rouaix, *Bull. Soc. Chim. France*, 687 (1958); K. Seki, J. Isegawa, M. Fukuda, and M. Ohki, *Chem. Pharm. Bull.*, 32, 1568 (1984)]. Treatment of 3 with methoxyamine hydrochloride in the presence of 3A molecular sieves [method based on that of T. Mukaiyama, R. Tsuzuki, and J. Kato, *Chem. Lett.*, 837 (1985)] selectively gives the 2-methoxime derivative 4. Reaction of 4 with the (bromomethyl)biphenylsulfonamide derivative 5 in the presence of potassium carbonate in a solvent such as DMF affords the desired alkylated product 6. When 6 is heated with the appropriate phenylhydrazine hydrochloride 7, preferably at about 100°–110° C. in acetic acid, optionally containing a cosolvent such as 2-methoxyethanol, a pyrazolecarboxylate 8 and/or 9 is isolated. This ring formation is highly regioselective. The t-butyl protecting group may be lost during the course of the reaction to give 9 directly. However, if the t-butyl product 8 (or a mixture of 8 and 9) is isolated, 8 is readily deprotected to yield 9 by treatment with trifluoroacetic acid in the presence of anisole. Acylation of the sulfonamide in 9 (for example, with an acid chloride in pyridine) yields the acylsulfonamide 10. Alternative acylation conditions may be employed. Thus, the use of an N-acylimidazole derivative (generated from the acid with 1,1'-carbonyldiimidazole) in the presence of DBU in THF is an especially effective method. Similarly, to prepare the sulfonylcarbamate 11, 9 is deprotonated with sodium hydride and treated with the appropriate chloroformate or dialkyl dicarbonate (the latter when $R^{24}$ is t-butyl).

SCHEME 2

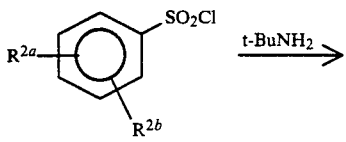

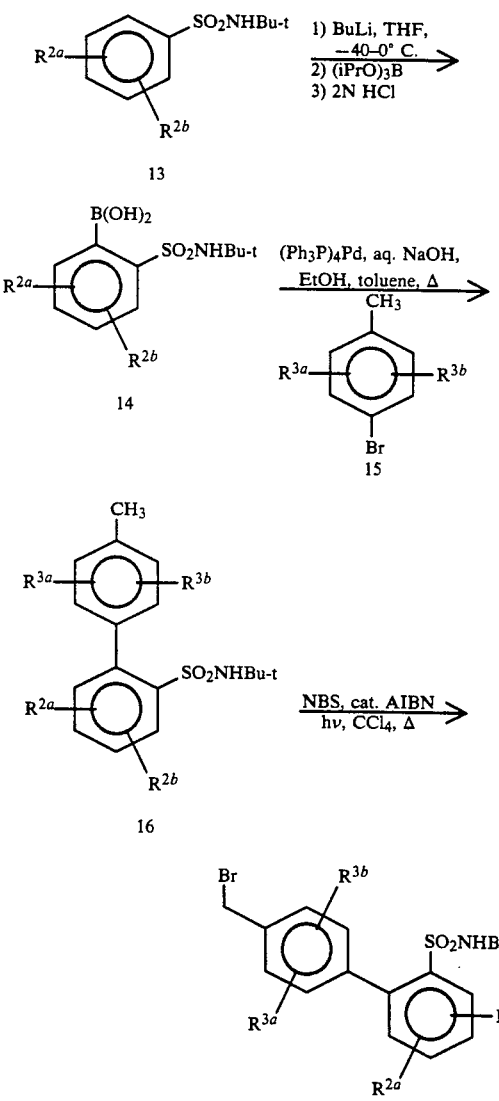

The synthesis of the biphenyl alkylating agent 5 is shown in Scheme 2. The benzenesulfonyl chloride 12 is first converted to the t-butylsulfonamide 13 by reaction with the amine. Based on a literature method [M. J. Sharp, W. Cheng, and V. Snieckus, *Tetrahedron Lett.*, 28, 5093 (1987)], metalation ortho to the sulfonamide is achieved with n-butyllithium in THF at −40° to 0° C. Then treatment with triisopropyl borate followed by acidic work-up affords the boronic acid 14. (It is understood that this method is appropriate when the $R^{2a}$ and $R^{2b}$ substituents do not themselves exert a directing effect that overrides that of the sulfonamide. The method is generally useful for alkyl or halogen substituents.) The boronic acid 14 undergoes cross-coupling with the 4-bromotoluene derivative 15 in the presence of tetrakis(triphenylphosphine)palladium(0) according to literature methods [M. J. Sharp, et al., op. cit.; N. Miyaura, T. Yanagi, and A. Suzuki, *Synth. Commun.*, 11, 513 (1981)] to give the biphenyl product 16. Bromination of the methyl group to give 5 can be carried out by photochemical bromination in the presence of an initiator such as AIBN or benzoyl peroxide.

SCHEME 3

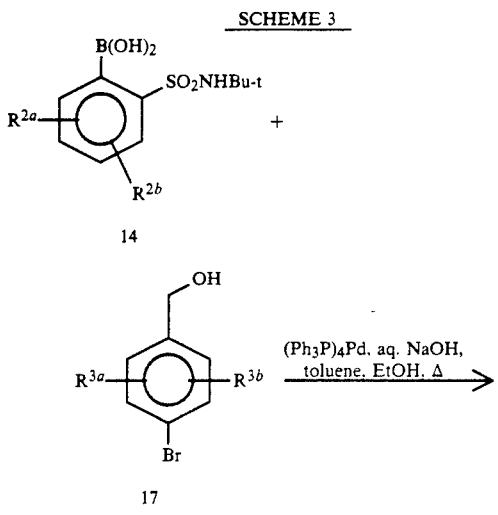

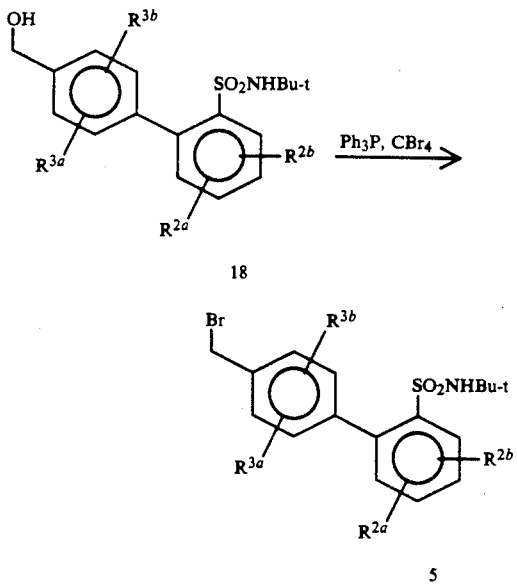

In a variation of Scheme 2 (shown in Scheme 3), the boronic acid 14 is coupled with the 4-bromobenzyl alcohol 17 to give the biphenylmethanol 18. The alcohol is then converted to the bromo compound 5 by standard methods, such as the use of triphenylphosphine and carbon tetrabromide. This method is valuable when one or more of the $R^2$ or $R^3$ substituents (for example, alkyl) is incompatible with the photochemical bromination step of Scheme 2.

SCHEME 4

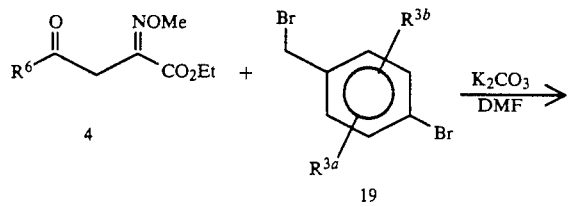

SCHEME 4

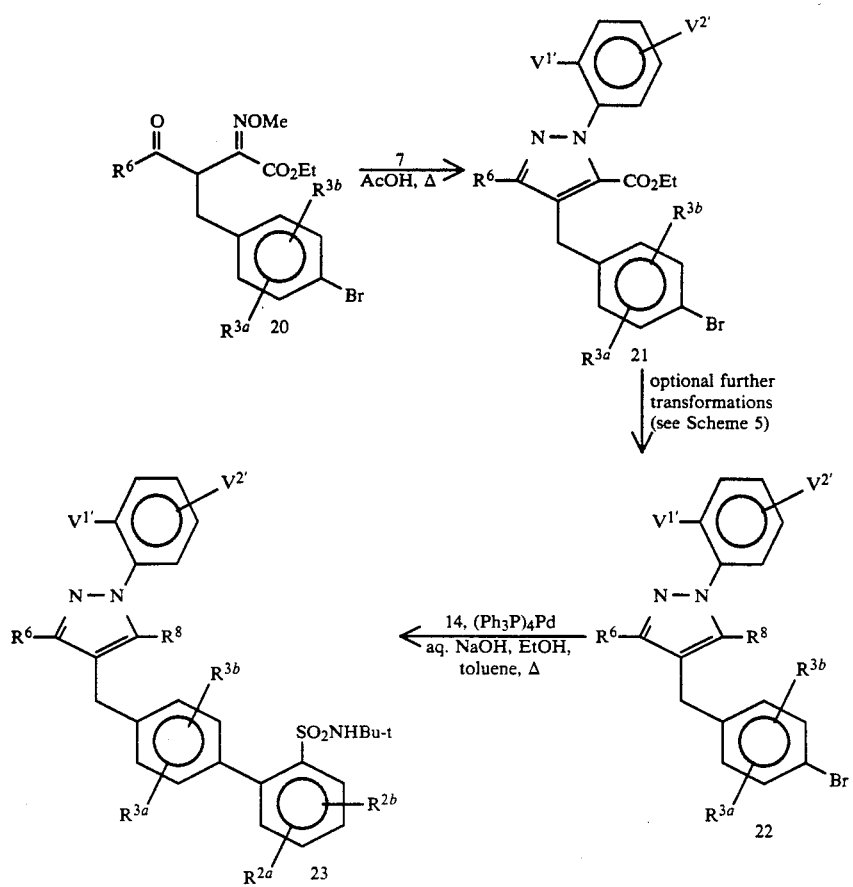

where $V^{1'}$ and $V^{2'}$ are $V^1$ and $V^2$, respectively, or precursors thereof An alternative approach to the synthesis of compounds of Formula I is to perform the biphenyl coupling after assembly of the pyrazole ring. As outlined in Scheme 4, the methoxime intermediate 4 is alkylated with the 4-bromobenzyl bromide 19 to provide 20. This is reacted with the arylhydrazine 7 as in Scheme 1 to give the pyrazolecarboxylate 21. At this point, further transformations at the $R^8$ position may be carried out (see Scheme 5). The resulting product 22 is coupled with the boronic acid 14 under the conditions described above to give the pyrazole 23, bearing the substituted biphenylmethyl side chain at the 4-position.

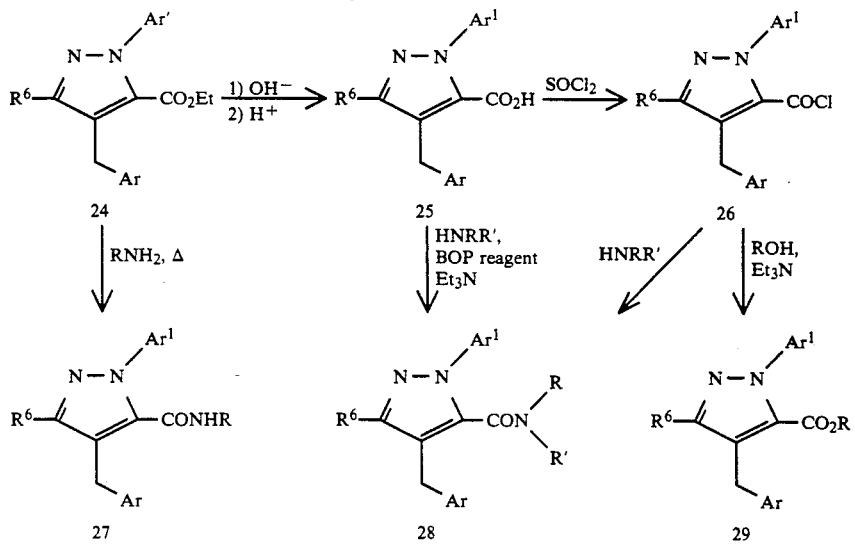

SCHEME 5

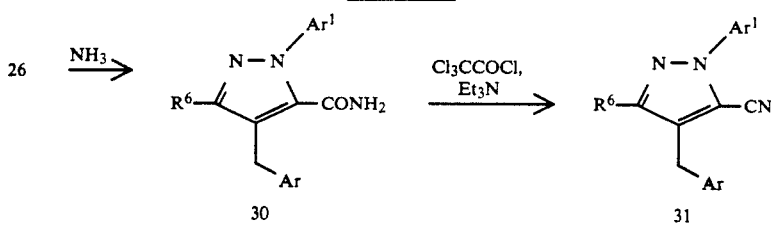

Scheme 5 illustrates transformations at $C^5$ of the pyrazole which may be used to introduce a variety of $R^8$ substituents. The pyrazolecarboxylate 24 (prepared as in earlier schemes) can be saponified under standard conditions to yield the carboxylic acid 25. Depending on the nature of other substituents, 25 may be converted to acid chloride 26 by reaction with thionyl chloride. For sufficiently reactive amines (especially primary aliphatic amines), the amide 27 is available by directly heating the ester 24 with the amine. A more versatile method to prepare amides of structure 28 consists of reacting the carboxylic acid 25 with an amine in the presence of a suitable coupling reagent such as BOP reagent (in the presence of a tertiary amine base) or DCC. Another route to 28 is the reaction of acid chloride 26 with the appropriate amine. Other esters 29 may be obtained by reacting 26 with an alcohol in the presence of triethylamine. The unsubstituted amide 30, obtained by treatment of 26 with ammonia, may be conveniently dehydrated to the nitrile 31 by use of trichloroacetyl chloride in the presence of triethylamine [A. Saedna, *Synthesis*, 184 (1985)].

SCHEME 6

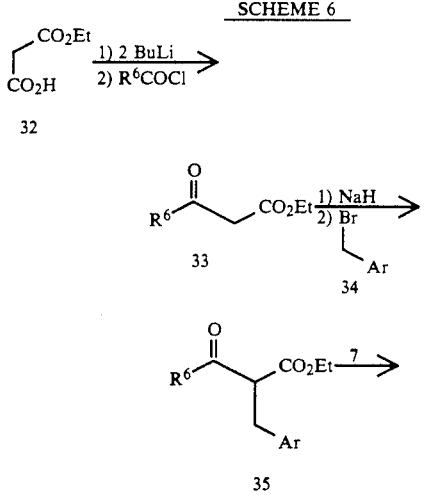

where $V^{1'}$ and $V^{2'}$ are $V^1$ and $V^2$, respectively, or precursors thereof.

The synthesis of compounds of Formula I wherein $R^8$ is hydroxy or alkoxy is shown in Scheme 6. Monoethyl malonate (32) is converted to a dianion by treatment with two equivalents of n-butyllithium and then reacted with the appropriate acid chloride to give the β-keto ester 33 [W. Wierenga and H. I. Skulnick, *Org. Synth.*, 61, 5 (1982)]. Alkylation of 33 with the appropriate arylmethyl bromide 34 to yield 35 is carried out under standard conditions, using a base such as sodium hydride in a solvent like DMF or DMSO. Condensation of 35 with the arylhydrazine 7 affords the hydroxypyrazole 36 (which may exist as a mixture of tautomers) [R. Fusco, in L. C. Behr, R. Fusco, and C. H. Jarboe, "Pyrazoles, Pyrazolines, Pyrazolidines, Indazoles and Condensed Rings" (R. H. Wiley, ed.), Interscience, New York, 1967, pp. 16-17]. In the presence of a base such as sodium hydride or sodium methoxide under anhydrous conditions, 36 can be alkylated to give the alkoxypyrazole 37 [R. Fusco, op. cit., pp. 130-131].

SCHEME 7

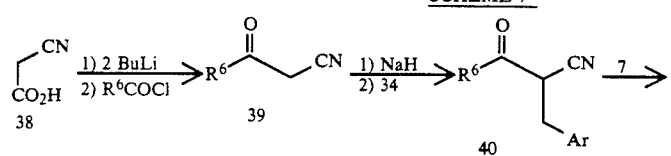

SCHEME 7 -continued

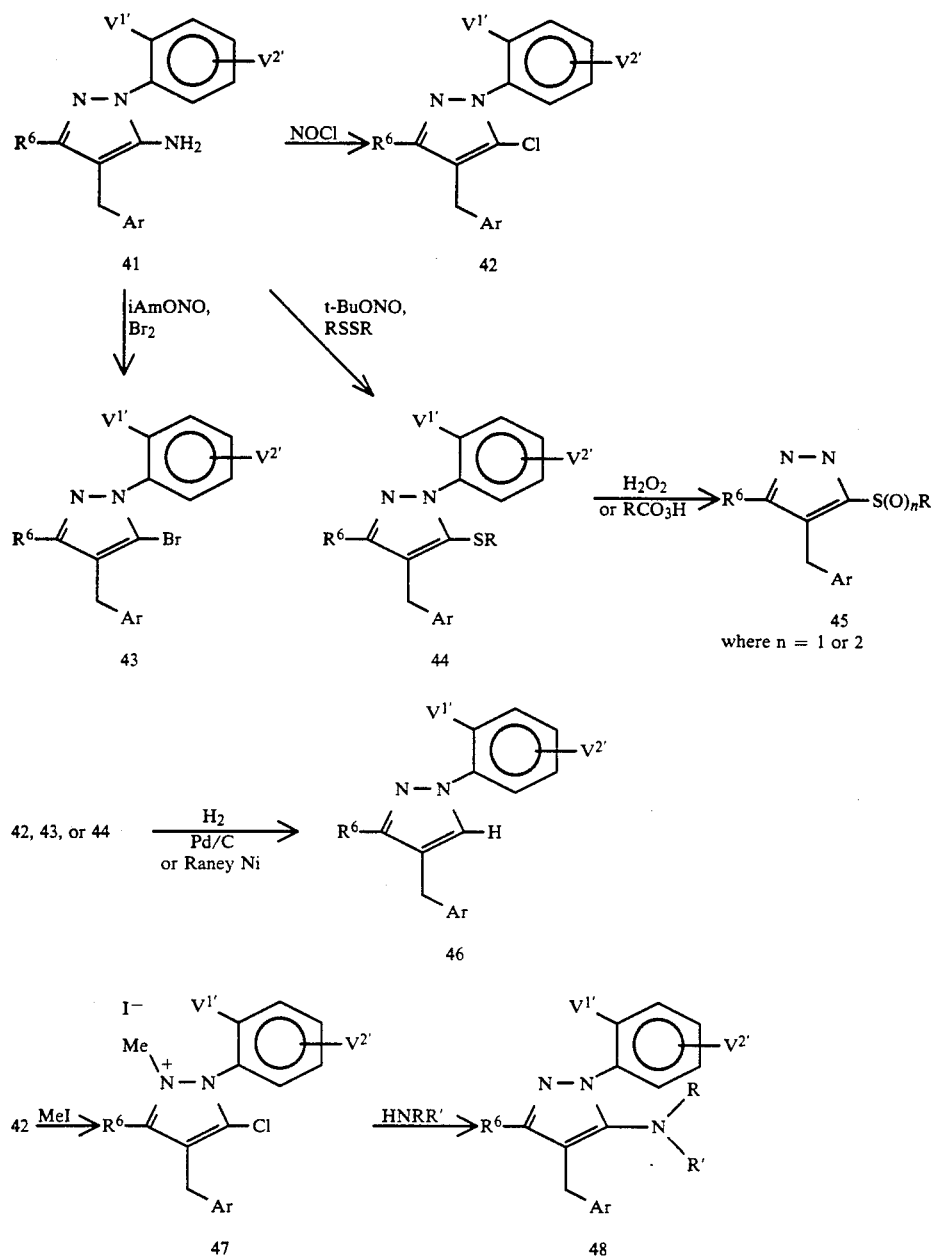

where $V^{1'}$ and $V^{2'}$ and $V^1$ and $V^2$, respectively, or precursors thereof.

Compounds of Formula I with various other $R^8$ substituents can be prepared according to Scheme 7. By methods analogous to those in Scheme 6, cyanoacetic acid (38) is acylated to give the β-keto nitrile 39 [J. C. Krauss, T. L. Cupps, D. S. Wise, and L. B. Townsend, *Synthesis*, 308 (1983)] and then alkylated with 34. The resulting product 40 can be condensed with the arylhydrazine 7 to yield aminopyrazole 41 [R. Fusco, op. cit., p. 16]. Using the chemistry of Beck [J. R. Beck, R. P. Gajewski, M. P. Lynch, and F. L. Wright, *J. Heterocycl. Chem.*, 24, 267 (1987); J. R. Beck, S. A. Ackmann, M. A. Staszak, and F. L. Wright, *J. Heterocycl. Chem.*, 25, 955 (1988)], 41 may be converted to the chloropyrazole 42 with nitrosyl chloride, to the bromopyrazole 43 with isoamyl nitrite and bromine, or to the (alkylthio)-pyrazole 44 with t-butyl nitite and a dialkyl disulfide. The thioether moiety of 44 can be further oxidized to a sufoxide or sulfone 45 using hydrogen peroxide or a peracid [R. Fusco, op. cit., p. 133; J. R. Beck, S. A. Ackmann, M. A. Staszak, and F. L. Wright, *J. Heterocycl. Chem.*, 25, 955 (1988)]. Introduction of hydrogen at the $R^8$ position may be accomplished by hydrogenolysis of 42, 43 or 44 in the presence of an appropriate catalyst such as palladium on carbon or Raney nickel [R. Fusco, op. cit., p. 89]. In addition, 42 may be treated with methyl iodide to give the N-alkylpyrazolium salt 47 [R. Fusco, op. cit., pp. 71-72]. Upon treatment with an amine, 47 may be converted (with accompanying dealkylation) to the aminopyrazole 48 [R. Fusco, op. cit., p. 104].

SCHEME 8
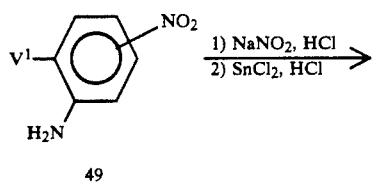
49
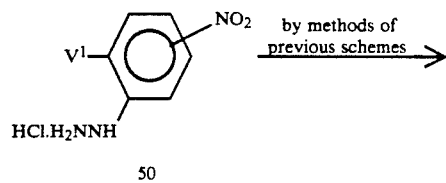
50
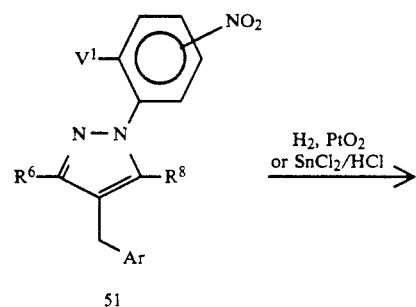
51
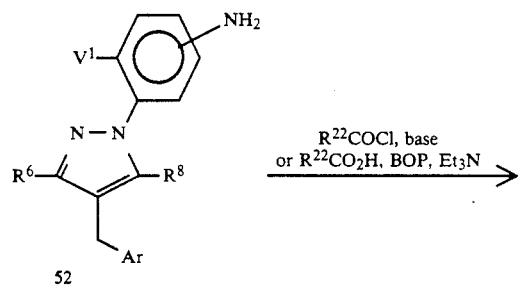
52
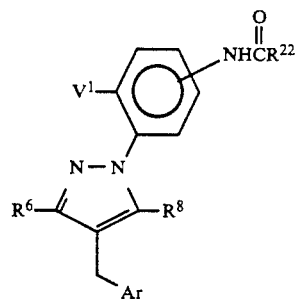
53

SCHEME 8

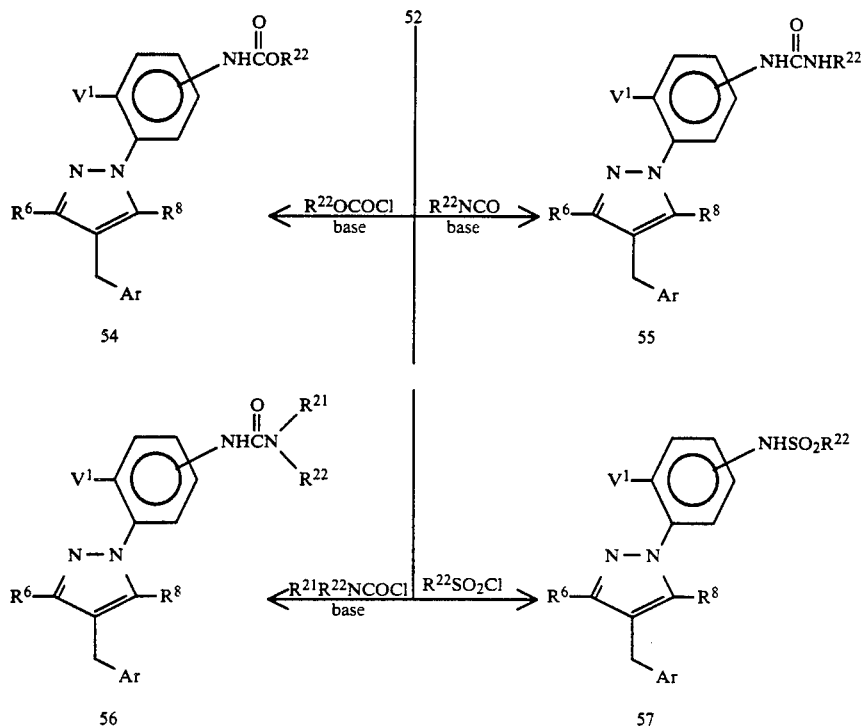

Transformations to generate various $V^2$ substituents of the substituted-amino type are illustrated in Scheme 8. The appropriately substituted nitroaniline is diazotized and then reduced with stannous chloride in the presence of hydrochloric acid to give the arylhydrazine hydrochloride 50 [H. Stroh and G. Westphal, *Chem. Ber.*, 96, 184 (1963)]. By the methods of the previous schemes, 50 is converted to the pyrazole 51. Reduction of the nitro group by hydrogenation in the presence of platinum oxide catalyst or by stannous chloride/hydrochloric acid yields the (aminophenyl)pyrazole 52. In the presence of a base such as sodium hydride, 52 can be reacted with an acid chloride to give the amide 53 (also accomplished by reacting 52 with a carboxylic acid in the presence of BOP reagent and triethylamine). Similarly, 52 may be reacted with a chloroformate to give a carbamate 54, with an isocyanate to give the urea 55, with a carbamoyl chloride to give a trisubstituted urea 56, or with a sulfonyl chloride to give the sulfonamide 57.

SCHEME 9

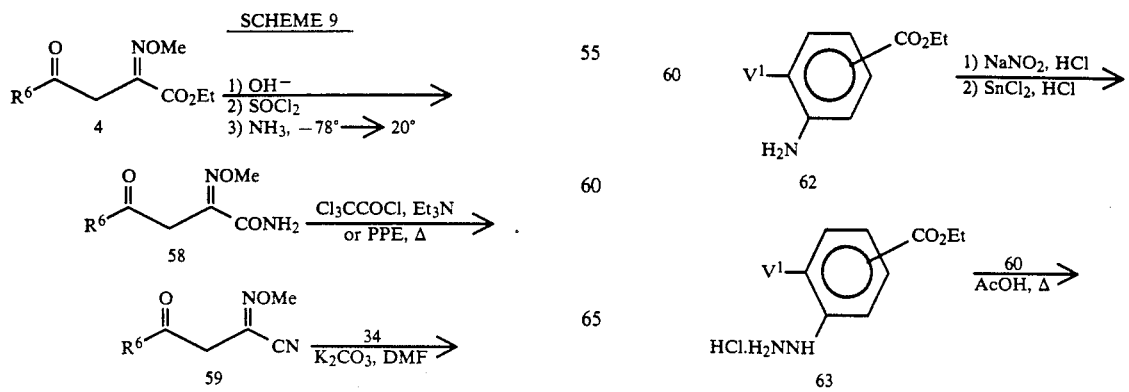

-continued
SCHEME 9

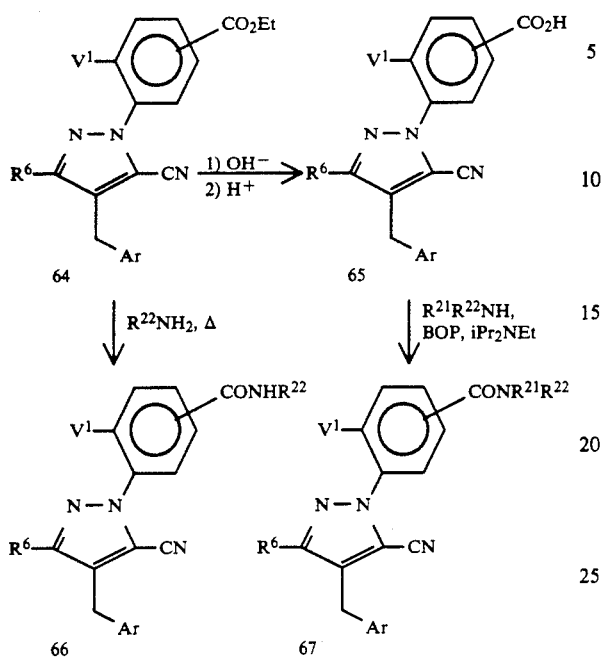

SCHEME 10

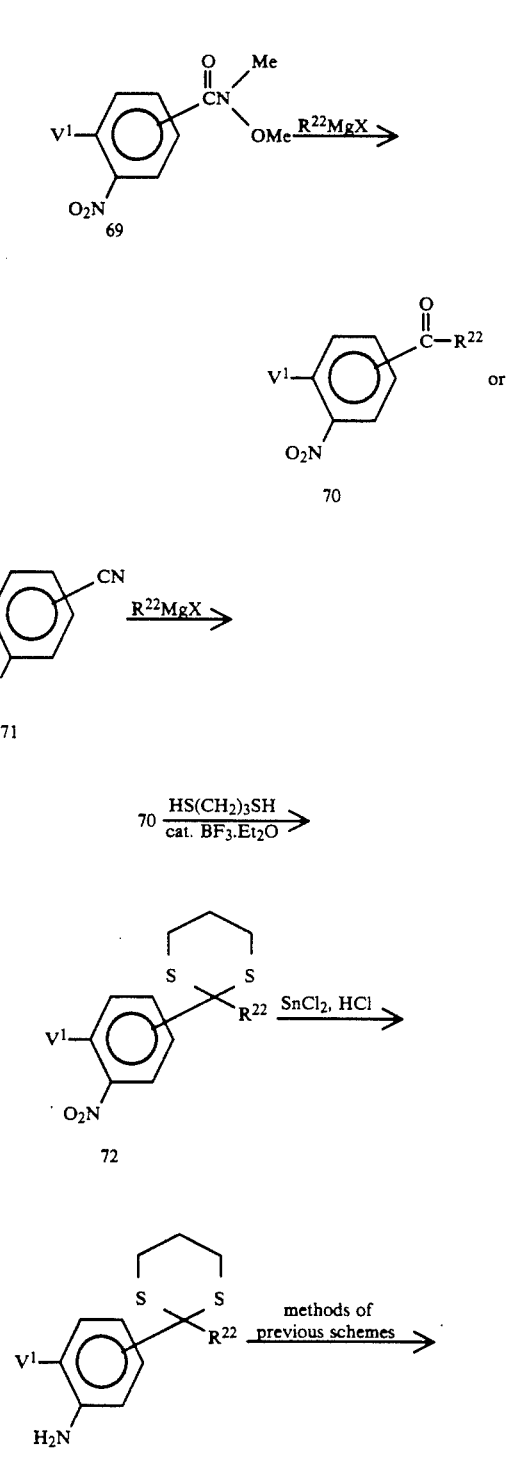

Additional $V^2$ substituents can be derived from an ester precursor on the aromatic ring. If $R^8$ were also a carboxylate, the differentiation of the two esters would be problematical. Scheme 9 shows how the problem can be circumvented in the case where $R^8$ is cyano by introducing the CN group before the pyrazole ring formation. The methoxime 4 is saponified with hydroxide under mild conditions, and the resulting acid is converted to the acid chloride with thionyl chloride. Treatment with anhydrous ammonia, initially at low temperature affords the amide 58, which is dehydrated to the nitrile 59 with trichloroacetyl chloride in the presence of triethylamine [A. Saedna, *Synthesis*, 184 (1985)]. Alternatively, 58 is dehydrated to 59 by heating with polyphosphate ester (PPE) [M. Cava, M. Lakshmikantham, and M. Mitchell, *J. Org. Chem.*, 34, 2665 (1969)] in alcohol-free chloroform according to a literature method [Y. Kanaoka, T. Kuga, and K. Tanizawa, *Chem. Pharm. Bull.*, 18, 397 (1971)]. Analogous to the methods of Scheme 1, 59 is alkylated with 34 to yield 60. In a variation of this approach, 4 is first alkylated with 34 to provide 61, and the ester is transformed to the nitrile as above, affording 60. Under carefully controlled conditions, the aminobenzoate ester 62 is diazotized and reduced (see Scheme 8) to give the arylhydrazine hydrochloride 63. Using conditions analogous to those in Scheme 1, 63 and 60 are condensed to give the pyrazolecarbonitrile 64. Saponification of the ester $V^2$ precursor yields the acid 65. It is possible to react 64 directly with sufficiently reactive amines (especially primary aliphatic amines) to provide the amide 66. Alternatively, the acid 65 is reacted with an amine (which may be disubstituted) in the presence of a coupling agent such as BOP reagent and a tertiary amine such as N,N-diisopropylethylamine or triethylamine, affording the amide 67.

SCHEME 10 -continued

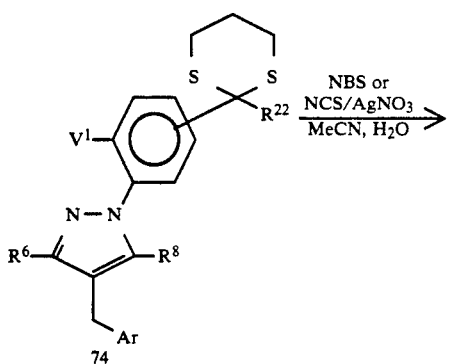

SCHEME 11

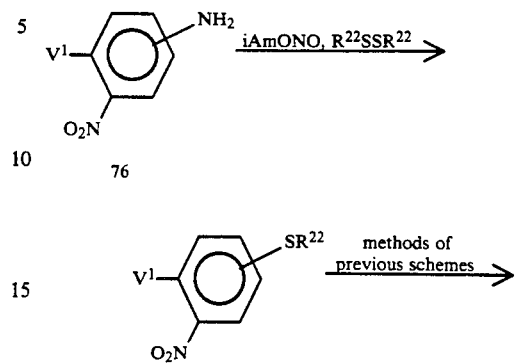

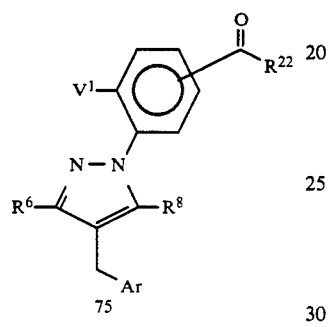

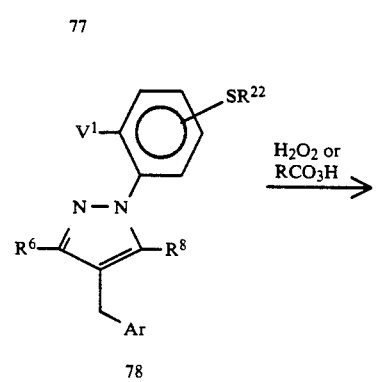

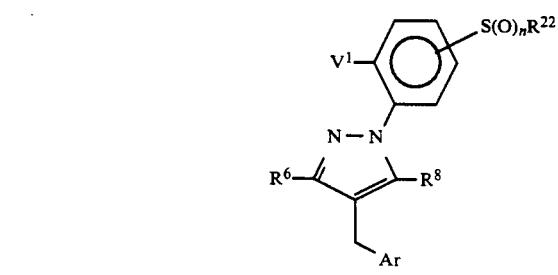

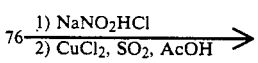

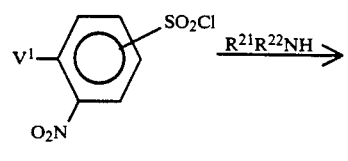

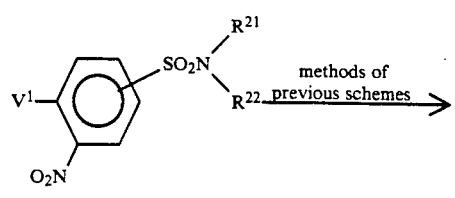

A strategy for introduction of a ketone substituent at the $V^2$ position is outlined in Scheme 10. The appropriate nitrobenzoic acid 68 may be treated with O,N-dimethylhydroxylamine in the presence of BOP reagent and N,N-diisopropylethylamine or triethylamine to furnish the N-methoxy-N-methylamide 69. (Intermediate 69 may also be obtained through the acid chloride of 68.) Following the Weinreb method [S. Nahm and S. M. Weinreb, *Tetrahedron Lett.*, 22, 3815 (1981)], 69 can be reacted with a Grignard reagent to afford the ketone product 70. Alternatively, 70 is obtained by treatment of the corresponding nitrobenzonitrile 71 with the Grignard reagent. In addition, certain compounds of structure 70 wherein the ketone group is para to $V^1$ are prepared by nitration of the pre-formed ketone (for example, by use of concentrated aqueous nitric acid at 0° C. [C. G. LeFevre and R. J. W. LeFevre, *J. Chem. Soc.*, 1988 (1932)]. This is most effective when the $V^1$ group directs the electrophilic substitution to an open ortho position, as is the case for chloro or bromo. The carbonyl group of 70 can then be protected as the dithiane by treatment of 70 with 1,3-propanedithiol in the presence of boron trifluoride etherate catalyst [J. A. Marshall and J. L. Belletire, *Tetrahedron Lett.*, 871 (1971)]. The nitro group of the resulting 72 is then reduced with stannous chloride in the presence of hydrochloric acid to give 73, which is converted to the pyrazole 74 by the methods of previous schemes. Finally, the dithiane is deprotected by one of various literature methods, such as the use of NBS (or a mixture of NCS and silver nitrate) in aqueous acetonitrile [E. J. Corey and B. W. Erickson, *J. Org. Chem.*, 36, 3553 (1971)], giving the ketone product 75.

-continued
SCHEME 11

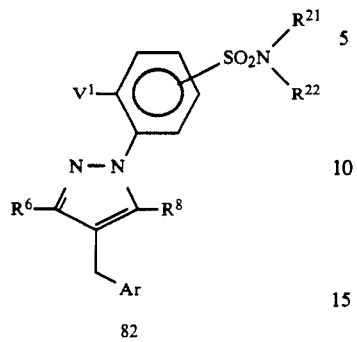

82

Illustrated in Scheme 11 are pathways to compounds of Formula I bearing sulfur-derived $V^2$ substituents. Thus, the nitroaniline 76 may be diazotized with isoamyl nitrite and treated with a disulfide to give a thioether 77 [C. S. Giam and K. Kikukawa, *J. Chem. Soc. Chem. Commun.*, 756 (1980)]. By the methods of previous schemes, 77 is transformed to the pyrazole 78. Conversion of 78 to a sulfoxide or sulfone 79 is accomplished with standard oxidizing methods (i.e., use of hydrogen peroxide or a peracid). Diazotization of the amine 76 and reaction of the diazonium salt with sulfur dioxide in the presence of cupric chloride affords the corresponding arylsulfonyl chloride 80 [see H. Meerwein, et al., *Chem. Ber.*, 90, 841 (1957); A. J. Prinsen and H. Cerfontain, *Rec. Trav. Chim.*, 84, 24 (1965); E. E. Gilbert, *Synthesis*, 3 (1969); and references cited therein]. Certain compounds of structure 80, such as 4-chloro-3-nitrobenzenesulfonyl chloride, are commercially available. Reaction of 80 with an amine (optionally in the presence of a base such as N,N'-diisopropylethylamine or DBU) yields the sulfonamide 81, which is transformed to the pyrazole 82 by the methods of the previous schemes. Intermediates of structure 81, where the sulfonamide is para to $V^1$ may also be prepared by nitration of a pre-formed sulfonamide.

SCHEME 12

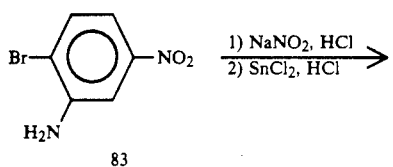

83

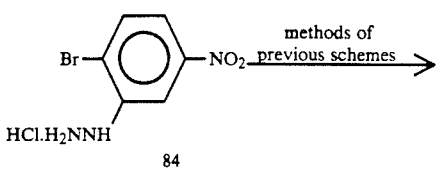

84

-continued
SCHEME 12

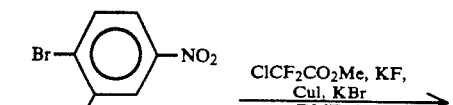

85

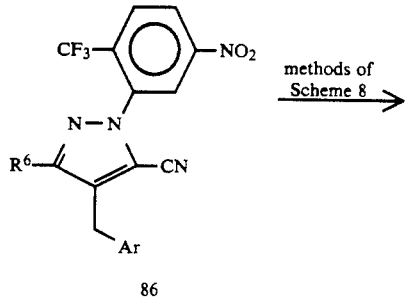

86

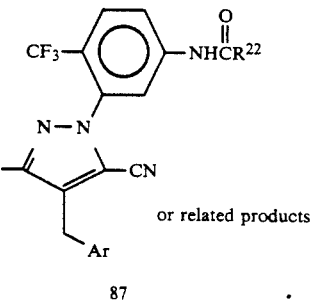

or related products

87

Because of the lack of appropriate commercial starting materials, special routes are required for the synthesis of some compounds of Formula I wherein $V^1$ is trifluoromethyl. One example is shown in Scheme 12. Diazotization of 2-bromo-5-nitroaniline (83) and reduction of the diazonium salt with stannous chloride/hydrochloric acid gives the arylhydrazine hydrochloride 84 [H. Stroh and G. Westphal, *Chem. Ber.*, 96, 184 (1963)]. The methods of the previous schemes are employed to convert 84 to a pyrazolecarbonitrile of structure 85. Based on literature conditions [D.-B. Su, J.-X. Duan, and Q.-Y. Chen, *Tetrahedron Lett.*, 32, 7689 (1991)], 85 is heated at about 120° C. with methyl chlorodifluoroacetate, cuprous iodide, potassium fluoride, and potassium bromide in DMF, resulting in displacement of bromo by trifluoromethyl to give 86. Normally this is accomplished at the stage of the N-(t-butyl)biphenylsulfonamide intermediate, as in 23. By the methods of Scheme 8, the 5-nitro substituent on the aromatic ring is converted into the acylamino derivative 87 or related products.

SCHEME 13

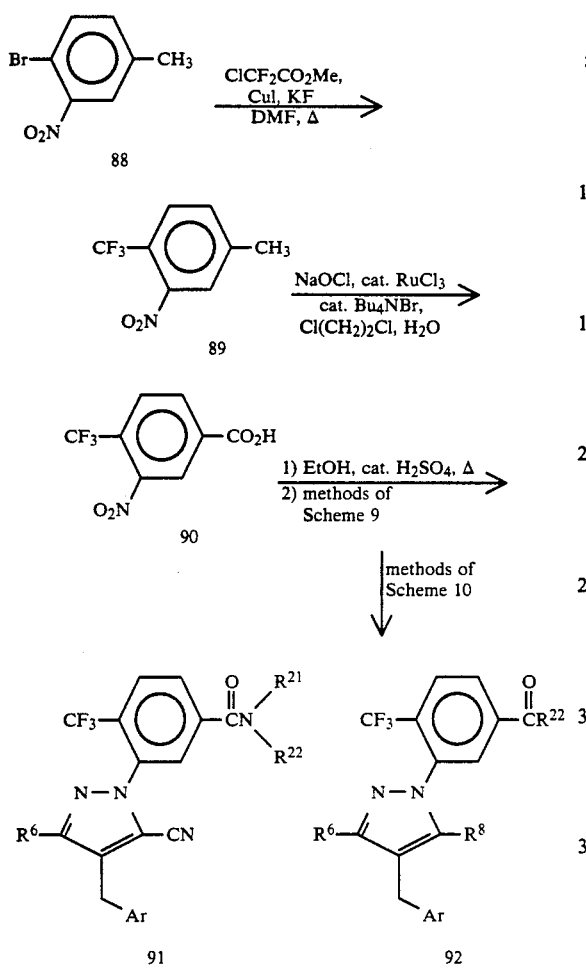

Scheme 13 shows the preparation of additional target compounds of Formula I wherein $V^1$ is trifluoromethyl and $V^2$ is a carboxamide or ketone substituent at the 5-position of the aromatic ring. By the method described above for Scheme 12, the commercially available 4-bromo-3-nitrotoluene (88) is converted to the corresponding trifluoromethyl compound 89. Oxidation of the methyl group with sodium hypochlorite and catalytic ruthenium trichloride in a two-phase system containing tetrabutylammonium bromide as a phase-transfer catalyst [Y. Sasson, G. D. Zappi, and R. Neumann, *J. Org. Chem.*, 51, 2880 (1986)] affords the carboxylic acid 90. Esterification of 90 (for example, by reaction with ethanol at reflux in the presence of catalytic sulfuric acid) followed by the methods of Scheme 9 affords the pyrazolecarbonitrile 91, which bears a carboxamide $V^2$ substituent. Likewise, by use of the methods of Scheme 10, 90 is transformed to the pyrazole 92 with a ketone $V^2$ substituent.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the $AT_1$ and $AT_2$ receptors. In order to identify AII antagonists and determine their efficacy in vitro, the following ligand-receptor binding assays were used along with binding assays reported in the literature (R. S. Chang et al. *Biochem. Biophys. Res. Commun.* 1990, 171, 813.).

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2 mg/ml Bacitracin and the suspension was used for 100 assay tubes. Samples tested for screening were done in duplicate. To the membrane preparation (0.25 ml) there was added $^{125}I$-Sar$^1$Ile$^8$-angiotensin II [obtained from New England Nuclear] (10 μl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-Sar$^1$Ile$^8$-antiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris•HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethanesulfonyl fluoride (PMSF) (0.1 mM)]. (For screening of compounds, generally duplicates of tubes are used). To the membrane preparation (0.5 ml) there was added $^3$H-angiotens II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using a Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

Receptor assay using rat brain membrane preparation

Membranes from rat brain (thalamus, hypothamus and midbrain) are prepared by homogenization in 50 mM Tris HCl (pH 7.4), and centrifuged at 50,000×g. The resulting pellets are washed twice in 100 mM NaCl, 5 mM $Na_2$•EDTA, 10 mM $Na_2HPO_4$ (pH 7.4) and 0.2 mM PMSF by resuspension and centrifugation. For binding assays, the pellets are resuspended in 160 volumes of binding assay buffer (100 mM NaCl, 10 mM $Na_2HPO_4$, 5 mM $Na_2$•EDTA, pH 7.4, 0.1 mM PMSF, 0.1 mg/ml soybean trypsin inhibitor, 0.018 mg/ml o-phenanthroline, 77 mg/ml dithiothreitol and 0.14 mg/ml bacitracin. For $^{125}$I-Ile$^8$-angiotensin II binding assays, 10 μl of solvent (for total binding), Sar$^1$, Ile$^8$-angiotensin II (1 μM) (for nonspecific binding) or test compounds (for displacement) and 10 μl of [$^{125}$I]Sar$^1$, Ile$^8$-angiotensin II (23–46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention were evaluated and were found to exhibit an activity of at least $IC_{50} < 50$ μM, in both the $AT_1$ and $AT_2$ angiotensin II receptor subtypes, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate-60 strokes per minute, volume-1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 5 to 150 mg. per patient per day.

The compounds of this invention can also be administered in combination with other antihypertensives and-/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidine sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

EXAMPLE 1

Ethyl 3-n-Butyl-4-[[2'-[N-(2-chlorobenzoyl)sulfamoyl]biphenyl-4-yl]methyl]-1-[2-chloro-5-(valerylamino)phenyl]-1H-pyrazole-5-carboxylate Step A: Ethyl 2-methoxyimino-4-oxooctanoate A mixture of 7.00 g (35 mmole) of ethyl 2,4-dioxooctanoate [K. Seki, J. Isegawa, M. Fukuda, and M. Ohki, *Chem. Pharm. Bull.*, 32 1568 (1984)], 3.07 g (36.75 mmol) of methoxyamine hydrochloride, 35 g of 3 Å molecular sieves, and 35 ml of dry EtOH was stirred vigorously at room temperature in a stoppered flask. After 21.5 hours, the mixture was filtered, and the filter cake was washed with EtOH. The combined filtrate and washings were concentrated in vacuo at $\leq 35°$ C. The residue was partitioned between 100 ml of Et$_2$O and 100 ml of saturated aqueous NaHCO$_3$ solution. The Et$_2$O layer was washed with 2×100 ml of H$_2$O, then filtered to remove some insoluble solid, and reseparated. The Et$_2$O phase was dried over MgSO$_4$, filtered, and concentrated in vacuo at <30° C. to give a reddish-orange residual oil. This material was chromatographed twice on silica gel (gradient elution, first with 3-7.5% and then 3-10% EtOAc in hexane) to yield, after vacuum-drying at room temperature, 4.14 g (52%) of very pale yellow residual oil, homogeneous by TLC in 4:1 hexane-EtOAc. 400 MHz $^1$H NMR (CDCl$_3$): $\delta$(ppm) 0.88 (t,J=7.1 Hz, 3H), 1.2-1.35 (m, 5H), 1.54 (m, 2H), 2.45 (t, J=7.3 Hz, 2H), 3.68 (s, 2H), 4.03 (s, 3H), 4.31 (q, J=6.8 Hz, 2H). FAB-MS: m/e 230 (M+H)$^+$.

Analysis (C$_{11}$H$_{19}$NO$_4$): Calcd: C, 57.62; H, 8.35; N, 6.11; Found: C, 57.65; H, 8.05; N, 6.05.

Note: In a similar preparation, the higher R$_f$ contaminant (removed by column chromatography) was isolated in 8% yield and identified as ethyl 2,4-bis(methoxyimino)octanoate, which by NMR appeared to exist as a pair of syn- and anti-isomers.

300 MHz $^1$H NMR (CDCl$_3$): $\delta$(ppm) 0.88, 0.89 (overlapping t, J=7.5 Hz, total 3H), 1.2-1.35 (m, 5H), 1.45 (m, 2H), 2.18, 2.26 (t, J=7.5 Hz, total 2H), 3.43, 3.44 (overlapping s, total 2H), 3.74, 3.75 (overlapping s total 3H), 4.02, 4.04 (overlapping s, total 3H), 4.31 4.32 (overlapping q, J=7.5 Hz, total 2H). FAB-MS: m/e 259 (M+H)$^+$.

Step B: 2-Bromo-N-(tert-butyl)benzenesulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 hours, then the mixture evaporated to dryness. Flash chromatography (silica gel, 15% ethyl acetate-hexane) afforded the title compound, (2.12 g, 84%) as a white solid; $^1$H NMR (300 MHz, CDCl$_3$) δ8.18 (d, J=8.5 Hz, 1H), 7.73 (d, J=8.5 Hz, 1H), 7.50–7.35 (m, 2H), 5.11 (s, 1H), 1.20 (s, 9H).

Step C: p-Tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 hours then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (bp 39°–40° C., 0.1 mm Hg) which was further purified by flash chromatography (silica gel, hexane) to give p-tolyltrimethyltin (7.30 g, 82%) as a colorless liquid; $^1$H NMR (300 MHz, CDCl$_3$) δ7.40 (d, J=7.7 Hz, 2H), 7.19 (d, J=7.7 Hz, 2H), 2.34 (s, 3H), 0.30 (s, 9H).

Step D: 2'-(N-t-Butylsulfamoyl)-4-methylbiphenyl

2-Bromo-N-(tert-butyl)benzenesulfonamide (from Step B) (1.00 g, 3.92 mmol), p-tolyltrimethyltin (from Step C) (1.95 g, 6.67 mmol), bis(triphenylphosphinepalladium(II) chloride (Aldrich) (165 mg, 0.235 mmol) and dimethylformamide (25 ml) were heated with stirring under nitrogen at 90° C. for 5 hours. The black suspension was cooled to room temperature, then filtered through a pad of Celite which was washed with tetrahydrofuran. The colorless filtrate was evaporated to dryness, then chromatographed (silica gel, 10% ethyl acetate-hexane) to give the title compound (0.88 g, 74%) as a white solid; $^1$H NMR (300 MHz, CDCl$_3$) δ8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step E: [2'-(N-t-Butylsulfamoyl)biphenyl-4-yl]methyl bromide

N-Bromosuccinimide (387 mg, 2.17 mmol), α,α'-azobis(isobutyronitrile) (catalytic), 2'-(N-t-butylsulfamol)-4-methylbiphenyl (from Step D) (550 mg, 1.81 mmol) and carbon tetrachloride (50 ml) were heated with stirring at reflux for 3 hours. After cooling to room temperature the mixture was filtered and the filtrate evaporated to dryness. Flash chromatography (silica gel, initially 10 and then 20% ethyl acetate-hexane) afforded the title compound [699 mg, 77% pure (the remainder of the material was the corresponding dibromo derivative), 97% yield] as a white solid; $^1$H NMR (300 MHz, CDCl$_3$) δ8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

Step F: Ethyl 3-[[2'-(N-t-Butylsulfamoyl)biphenyl-4-yl]methyl]-2-methoxyimino-4-oxooctanoate A mixture of 50 mg (0.218 mmol) of ethyl 2-methoxyimino-4-oxooctanoate (from Step A), 83 mg (0.218 mmol) of [2'-(N-t-butylsulfamoyl)biphenyl-4-yl]methyl bromide (from Step E), 36 mg (0.262 mmol) of freshly pulverized anhydrous potassium carbonate, and 0.6 mL of dry DMF was stirred vigorously for 24 hours at room temperature at which time the starting material was all consumed [TLC (5:1 hexane/EtOAc)]. The mixture was partitioned between 10 mL of EtOAc and 10 mL of 0.2N HCl. The EtOAc layer was then washed with 3×10 mL H$_2$O, 1×5 mL brine, and dried briefly over anhydrous sodium sulfate. The filtrate, obtained from filtration over sintered glass, was concentrated to dryness and the resulting residue was flash chromatographed over 20 mL silica gel (column packed using hexane, sample introduced as a solution in CH$_2$Cl$_2$) eluting with 20/1 hexane/ethyl acetate, to give 83 mg (71%) of the desired product as an oil, homogeneous by TLC. R$_f$=0.35 in 5:1 hexane/EtOAc. $^1$H NMR (200 MHz, CDCl$_3$, ppm)=δ0.88 (t, J=7.2 Hz, 3H), 1.00 (s, 9H), 1.31 (m, 5H), 1.52 (m, 2H), 2.32 (t, J=7.0 Hz, 2H), 3.03 (m, 1H), 3.40 (m, 1H), 3.61 (s, 1H), 4.04 (s, 3H), 4.25 (m, 3H), 7.16–7.52 (m, 7H), 8.15 (m, 1H), Mass spectrum: FAB (m/e) 531 (M+1)+.

Step G: Ethyl 3-n-Butyl-1-(2-chloro-5-nitrophenyl)-4-[(2'-sulfamoylbiphenyl-4-yl)methyl]-1H-pyrazole-5-carboxylate A mixture of 3.07 g (5.79 mmol) of ethyl 3-[[2'-(N-t-butylsulfamoyl)biphenyl-4-yl]methyl]-2-methoxyimino-4-oxooctanoate (from Step F), 5.00 g (22.3 mmol) of 2-chloro-5-nitrophenylhydrazine hydrochloride [prepared from 2-chloro-5-nitroaniline according to H. Stroh and G. Westphal, Chem. Ber., 96, 184 (1963)], 55 mL of glacial acetic acid, and 25 mL of 2-methoxyethanol was stirred under N$_2$ at 105° C. for 20 hours. The cooled mixture was concentrated in vacuo and the residue was partitioned between 200 mL of 0.2N HCl and 200 mL of ethyl acetate. The organic layer was washed with H$_2$O (200 mL), dried over Na$_2$SO$_4$, filtered, and concentrated. Flash chromatography of the residue twice on silica gel (first column eluted with 2% MeOH in CH$_2$Cl$_2$, second column eluted with 1% MeOH in CH$_2$Cl$_2$) to provide 1.71 g (47%) of the title compound as a viscous, orange oil; homogeneous by TLC in 98:2 CH$_2$Cl$_2$—MeOH; mass spectrum (FAB) m/e 598 (M+1)+. 400 MHz $^1$H NMR (CDCl$_3$) δ0.87 (t, J=7.3 Hz, 3H), 1.06 (t, J=7.1 Hz, 3H), 1.34 (m, 2H), 1.59 (m, 2H, partially obscured by H$_2$O peak), 2.62 (t, J=7.8 Hz, 2H), 4.10 (s, 2H), overlapping 4.14 (q, J=7.0 Hz, 2H), 4.24 (s, 2H), 7.26 (d, J=8.2 Hz, 2H), 7.32 (dd, J=7.5, 1.3 Hz, 1H), 7.41 (d, J=8.2 Hz, 2H), 7.49 (m, 1H), 7.58 (m, 1H), 7.66 (d, J=8.8 Hz, 1H), 8.14 (dd, J=7.9, 1.3 Hz, 1H), 8.26 (dd, J=8.8, 2.7 Hz, 1H), 8.36 (d, J=2.6 Hz, 1H).

Analysis [C$_{29}$H$_{29}$ClN$_4$O$_6$S.0.5C$_3$H$_8$O$_2$ (2-methoxyethanol)]: Calcd: C, 57.68; H, 5.24; N, 8.82. Found: C, 57.46; H, 5.18; N, 8.48.

Step H: Ethyl 3-n-Butyl-4-[[2'-[N-(2-chlorobenzoyl)sulfamoyl]-biphenyl-4-yl)methyl]-1-(2-chloro-5-nitrophenyl)-1H-pyrazole-5-carboxylate A mixture of 675 mg (4.28 mmol) of 2-chlorobenzoic acid, 695 mg (4.28 mmol) of 1,1'-carbonyldiimidazole (CDI), and 2 mL of dry THF was stirred at 50° C. under N$_2$ for 3 hours. Then a solution of 851 mg (1.43 mmol) of ethyl 3-n-butyl-1-(2-chloro-5-nitrophenyl)-4-[(2'-sulfamoylbiphenyl-4-yl)methyl]-1H-pyrazole-5-carboxylate (from Step G) and 640 μL (651 mg, 4.28 mmol) of 1,8-diazabicyclo[5.4.0]-undec-7-ene (DBU) in 5 mL of dry THF was added, and stirring under N$_2$ at 50° C. was continued overnight. The cooled reaction mixture was partitioned between 75 mL of 5% citric acid (aqueous) and 75 mL of ethyl acetate. The organic phase was washed with H$_2$O, dried (Na$_2$SO$_4$), filtered, and concentrated. The orange residue was flash chromatographed on silica gel (elution with 1% MeOH in CH$_2$Cl$_2$) to yield 503 mg (48%) of the title compound as a solid, mp>60° C. (gradual); homogeneous by TLC in 95:5 CH$_2$Cl$_2$—MeOH; mass spectrum (FAB) m/e 736 (M+1)+. 400 MHz $^1$H NMR (CDCl$_3$) δ0.88 (t, J=7.3

Hz, 3H), 1.05 (t, J=7.1 Hz, 3H), 1.34 (m, 2H), 1.59 (m, 2H, partially obscured by H₂O peak), 2.56 (t, J=7.8 Hz, 2H), 4.14 (q, J=7.1 Hz, 2H), overlapping 4.16 (s, 2H), 7.07 (d, J=8.1 Hz, 2H), 7.25–7.45 (m, 6H), 7.55–7.69 (m, 4H), 8.26 (dd, J=8.8, 2.6 Hz, 1H), 8.35 (dd, J=8.1, 1.3 Hz, 2H).

Analysis ($C_{36}H_{32}Cl_2N_4O_7S \cdot 0.25H_2O$): Calcd: C, 58.42; H, 4.43; N, 7.57. Found: C, 58.14; H, 4.42; N, 7.25.

Step I: Ethyl 1-(5-Amino-2-chlorophenyl)-3-n-butyl-4-[[2'-[N-(2-chlorobenzoyl)sulfamoyl]biphenyl-4-yl]methyl]-1H-pyrazole-5-carboxylate A mixture of 450 mg (0.612 mmol) of ethyl 3-n-butyl-4-[[2'-[N-(2-chlorobenzoyl)sulfamoyl]biphenyl-4-yl]methyl]-1-(2-chloro-5-nitrophenyl)-1H-pyrazole-5-carboxylate (from Step H), 50 mg of platinum oxide and 80 mL of ethanol was shaken with hydrogen at 3–4 atm for 1.25 hours. The catalyst was removed by filtration through Celite, and the filtrate was concentrated in vacuo to yield 401 mg (93%) of the title compound as a tan solid, mp>75° C. (gradual); nearly homogeneous by TLC in 95:5 CH₂Cl₂—MeOH; mass spectrum (FAB) m/e 705 (M+1)⁺. 400 MHz ¹H NMR (DMSO-d₆) δ0.81 (t, J=7.4 Hz, 3H), 0.97 (t, J=7.1 Hz, 3H), 1.25 (m, 2H), 1.48 (m, 2H), 2.49 (t, 2H, partially obscured by DMSO peak), 4.0–4.2 (m, 4H), 5.5 (v br m, 2H), 6.64 (m, 2H), 7.1–7.4 (m, 8H), 7.47 (m, 2H), 7.6–7.75 (m, 2H), 8.16 (dd, J=8.0, 1.1 Hz, 1H).

Step J: Ethyl 3-n-Butyl-4-[[2'-[N-(2-chlorobenzoyl)-sulfamoyl]-biphenyl-4-yl]methyl]-1-[2-chloro-5-(valerylamino)phenyl]-1H-pyrazole-5-carboxylate To a mixture of 150 mg (0.213 mmol) of ethyl 1-(5-amino-2-chlorophenyl)-3-n-butyl-4-[[2'-[N-(2-chlorobenzoyl)sulfamoyl]-biphenyl-4-yl]methyl]-1H-pyrazole-5-carboxylate (from Step I), 26 mg (0.213 mmol) of 4-(dimethylamino)pyridine (DMAP), and 1.75 mL of dry pyridine was added 126 μL (128 mg, 1.06 mmol) of valeryl chloride. The mixture was stirred under N₂ at room temperature overnight and then partitioned between H₂O and ethyl acetate. The organic layer was washed twice with H₂O and then with brine. Next, the ethyl acetate phase was dried over Na₂SO₄, filtered, and rotary-evaporated in vacuo. The yellow-orange residual oil was flash chromatographed on silica gel (gradient elution with 0.5–3% MeOH in CH₂Cl₂) to give 123 mg (72%) of the title compound as a slightly yellow solid, mp>95° C. (gradual); homogeneous by TLC in 95:5 CH₂Cl₂—MeOH; mass spectrum (FAB) m/e 827 (M+K)⁺. 400 MHz ¹H NMR (CDCl₃) δ0.87 (t, J=7.3 Hz, 3H), 0.92 (t, J=7.4 Hz, 3H), 1.02 (t, J=7.1 Hz, 3H), 1.29–1.40 (m, 4H), 1.57 (m, 2H), 1.67 (m, 2H), 2.32 (t, J=7.6 Hz, 2H), 2.53 (t, J=7.8 Hz, 2H), 4.05–4.15 (m, 4H), 7.06 (d, J=8.2 Hz, 2H), 7.21–7.66 (m, 10H), 7.75 (d, J=2.4 Hz, 1H), 8.27 (s, 1H), 8.34 (dd, J=8.0, 1.3 Hz, 1H).

Analysis ($C_{41}H_{42}Cl_2N_4O_6S \cdot 0.5H_2O$): Calcd: C, 61.65; H, 5.43; N, 7.02. Found: C, 61.63; H, 5.35; N, 6.89.

EXAMPLE 2

3-n-Butyl-4-[[2'-[N-(2-chlorobenzoyl)sulfamoyl]biphenyl-4-yl]methyl]-1-[2-chloro-5-(valerylamino)phenyl]-1H-pyrazole-5-carboxylic Acid A mixture of 39.5 mg (0.05 mmol) of ethyl 3-n-butyl-4-[[2'-[N-(2-chlorobenzoyl)sulfamoyl]biphenyl-4-yl]methyl]-1-[2-chloro-5-(valerylamino)phenyl]-1H-pyrazole-5-carboxylate (from Example 1), 200 μL (0.5 mmol) of 2.5N NaOH, and 600 μL of methanol was stirred under N₂ at 60° C. for 2 hours. The solution was cooled, diluted with 5 mL of H₂O, and adjusted to approximately pH 2 by gradual addition of 2N HCl, resulting in precipitation. The precipitate was collected on a filter and dried to yield 37.8 mg (97%) of the title compound as a nearly white solid, mp>110° C. (gradual); homogeneous by TLC in 9:1 CH₂Cl₂—MeOH; mass spectrum (FAB) m/e 761 (M+1)⁺. 400 MHz ¹H NMR (DMSO-d₆) δ0.80 (t, J=7.3 Hz, 3H), 0.88, (t, J=7.3 Hz, 3H), 1.24, 1.31 (overlapping m, each 2H), 1.47 (m, 2H), 1.57 (m, 2H), 2.31 (t, J=7.4 Hz, 2H), 2.48 (t, 2H, partially obscured by DMSO peak), 4.18 (br, 2H), 7.09 (d, J=7.4 Hz, 1H), 7.21 (d, J=8.3 Hz, 2H), 7.27–7.74 (m, 10H), 7.87 (d, J=2.5 Hz, 1H), 8.17 (dd, J=8.0, 1.3 Hz, 1H).

Analysis ($C_{39}H_{38}Cl_2N_4O_6S \cdot H_2O$): Calcd: C, 60.08; H, 5.17; N, 7.19. Found: C, 59.75; H, 4.88; N, 7.10.

EXAMPLE 3

3-n-Butyl-4-[[2'-[N-(2-chlorobenzoyl)sulfamoyl]biphenyl-4-yl]methyl]-1-[2-chloro-5-(valerylamino)phenyl]-1H-pyrazole-5-(N-methylcarboxamide)

A mixture of 43.6 mg (0.0552 mmol) of ethyl 3-n-butyl-4-[[2'-[N-(2-chlorobenzoyl)sulfamoyl]biphenyl-4-yl]methyl]-1-[2-chloro-5-(valerylamino)phenyl]-1H-pyrazole-5-carboxylate (from Example 1) and 8 mL of 40% methylamine (aqueous) was stirred at gentle reflux under N₂ for 24 hours and then concentrated to dryness. The yellow residue was purified by semipreparative HPLC on a Zorbax C8 reverse phase column (elution with 70:30 acetonitrile-H₂O containing 0.1% TFA) to give 23 mg (54%) of the title compound as a white, stiff foam, mp>60° C. (gradual); homogeneous by TLC in 90:10:1 CH₂Cl₂—MeOH—AcOH; mass spectrum (FAB) m/e 774 (M+1)⁺. 400 MHz ¹H NMR (DMSO-d₆) δ0.81 (t, J=7.3 Hz, 3H), 0.88, (t, J=7.4 Hz, 3H), 1.21–1.34 (m, 4H), 1.47, (m, 2H), 1.56 (m, 2H), 2.31 (t, J=7.4 Hz, 2H), 2.46 (t, J≈7.5 Hz, 2H, partially obscured by DMSO peak), 2.59 (d, J=4.6 Hz, 3H), 4.01 (s, 2H), 7.1–7.5 (m, 10H), 7.57 (dd, J=8.8, 2.5 Hz, 1H), 7.65 (m, 1H), 7.73 (m, 1H), 7.88 (d, J=2.5 Hz, 1H), 8.16 (dd, J=8.0, 1.3 Hz, 1H), overlapping 8.21 (q, J=4.6 Hz, 1H).

EXAMPLE 4

3-n-Butyl-4-[[2'-[N-(2-chlorobenzoyl)sulfamoyl]-3-fluorobiphenyl-4-yl]methyl]-1-[2-chloro-5-(propionylamino)phenyl]-1H-pyrazole-5-carbonitrile Step A: Ethyl 3-(4-Bromo-2-fluorobenzyl)-2-methoxyimino-4-oxooctanoate A mixture of 5.0 g (21.8 mmol) of ethyl 2-methoxyimino-4-oxooctanoate (from Example 1, Step A), 3.6 g (26 mmol) of anhydrous potassium carbonate, and 70 mL of dry DMF was stirred under N₂ at room temperature for 1 hour. The mixture was then cooled to 0° C. and treated dropwise with a solution of 5.9 g (21.8 mmol) of 4-bromo-2-fluorobenzyl bromide in 20 mL of dry DMF. The mixture was allowed to warm slowly to room temperature and was stirred under N₂ for 48 hours. The mixture was partitioned between 400 mL of ethyl acetate and 400 mL of 0.2N HCl. The organic layer was washed twice with H₂O and then dried over Na₂SO₄. The filtered solution was concentrated, and the residual oil was flash chromatographed on silica gel. Gradient elution with 5–20% ethyl acetate in hexane afforded 3.51 g (39%) of the title compound as an oil; homogeneous by TLC in 3:1 hexane-EtOAc; mass spectrum (FAB) m/e 416, 418 (M+1)⁺. 200 MHz ¹H NMR (CDCl₃) δ0.87 (t, J=7.1 Hz, 3H), 1.2–1.4 (m, 5H) including 1.25 (t, J=7.1 Hz, 3H), 1.55 (m, 2H), 2.31 (t, J=7.1 Hz, 2H), 2.97 (dd, J=14, 10 Hz, 1H), 3.36 (dd, J=14, 5 Hz, 1H), 3.95 (s, 3H), 4.15-4.35 (m, 3H), 6.98 (dd, J≈8, 8 Hz, 1H), 7.15 (apparent d, J=8.2 Hz, 2H).

Analysis ($C_{18}H_{23}BrFNO_4$): Calcd: C, 51.93; H, 5.57; N, 3.37. Found: C, 51.80; H, 5.27; N, 3.27.

Step B: Ethyl 4-(4-Bromo-2-fluorobenzyl)-3-n-butyl-1-(2-chloro-5-nitrophenyl)-1H-pyrazole-5-carboxylate By the procedure of Example 1, Step G, ethyl 3-(4-bromo-2-fluorobenzyl)-2-methoxyimino-4-oxooctanoate (from Step A) was reacted with 2-chloro-5-nitrophenylhydrazine hydrochloride. The crude product was flash chromatographed twice on silica gel (first column: gradient elution with 0.5-2% MeOH in $CH_2Cl_2$; second column: gradient elution with 5-20% EtOAc in hexane) to give a 54% yield of the title compound as an orange oil; homogeneous by TLC in 3:1 hexane-EtOAc; mass spectrum (FAB) m/e 538, 540 (M+1)+. 400 MHz $^1$H NMR (CDCl$_3$) δ0.86 (t, J=7.3 Hz, 3H), 1.02 (t, J=7.1 Hz, 3H), 1.32 (m, 2H), 1.55 (m, 2H, partially obscured by H$_2$O peak), 2.57 (t, J=7.8 Hz, 2H), 4.10 (s, 2H, superimposed on q, J=7.2 Hz, 2H), 6.82 (dd, J≈8, 8 Hz, 1H), 7.16 (d, J≈8 Hz, 1H), 7.23 (m, 1H, partially obscured by CHCl$_3$ peak), 7.65 (d, J=8.8 Hz, 1H), 8.25 (dd, J=8.8, 2.6 Hz, 1H), 8.33 (d, J=2.6 Hz, 1H).

Analysis ($C_{23}H_{22}BrClFN_3O_4$): Calcd: C, 51.27; H, 4.12; N, 7.80. Found: C, 50.99; H, 4.08; N, 7.83.

Step C: 4-(4-Bromo-2-fluorobenzyl)-3-n-butyl-1-(2-chloro-5-nitrophenyl)-1H-pyrazole-5-carboxylic Acid This material was prepared from ethyl 4-(4-bromo-2-fluorobenzyl)-3-n-butyl-1-(2-chloro-5-nitrophenyl)-1H-pyrazole-5-carboxylate (from Step B) according to the procedure of Example 2. However, upon acidification to pH 2, the product separated as a gum, which was extracted 3× with methylene chloride. The combined extracts were concentrated to give an 86% yield of the title compound as a yellow, stiff foam, mp>55° C. (gradual); homogeneous by TLC in 95:5 $CH_2Cl_2$—MeOH; mass spectrum (FAB) m/e 510, 512 (M+1)+. 400 MHz $^1$H NMR (DMSO-d$_6$) δ0.78 (t, J=7.3 Hz, 3H), 1.23 (m, 2H), 1.42 (m, 2H), 2.48 (m, 2H, obscured by DMSO peak), 4.10 (s, 2H), 7.01 (dd, J≈8.5, 8.5 Hz, 1H), 7.33 (d, J=8.1 Hz, 1H), 7.52 (dd, J=9.7, 1.8 Hz, 1H), 7.93 (d, J=8.9 Hz, 1H), 8.34 (dd, J=8.8, 2.6 Hz, 1H), 8.41 (br m, 1H).

Analysis ($C_{21}H_{18}BrClFN_3O_4$): Calcd: C, 49.38; H, 3.55; N, 8.23. Found: C, 49.26; H, 3.39; N, 8.26.

Step D: 4-(4-Bromo-2-fluorobenzyl)-3-n-butyl-1-(2-chloro-5-nitrophenyl)-1H-pyrazole-5-carbonyl Chloride A mixture of 672 mg (1.32 mmol) of 4-(4-bromo-2-fluorobenzyl)-3-n-butyl-1-(2-chloro-5-nitrophenyl)-1H-pyrazole-5-carboxylic acid (from Step C), 2.3 mL of thionyl chloride, and 6 mL of cyclohexane was stirred at reflux under N$_2$ for 4 hours, during which time HCl gas was evolved. The cooled solution was concentrated in vacuo to yield an orange oil, which was used directly in the next step.

Step E: 4-(4-Bromo-2-fluorobenzyl)-3-n-butyl-1-(2-chloro-5-nitrophenyl)-1H-pyrazole-5-carboxamide A solution of 4-(4-bromo-2-fluorobenzyl)-3-n-butyl-1-(2-chloro-5-nitrophenyl)-1H-pyrazole-5-carbonyl chloride (from Step D, theoretically 1.32 mmol) in 10 mL of dry THF was cooled to −50° C. and maintained at that temperature under protection from moisture as ammonia gas was gently bubbled in until saturated. The mixture was allowed to warm slowly to room temperature and stirred overnight. Concentration of the reaction mixture yielded a thick yellow oil, which was purified by flash chromatography on silica gel (elution with 1% and then 3% MeOH in $CH_2Cl_2$). Evaporation of the pooled product fractions yielded 625 mg (93%) of the title compound as a slightly yellow solid, mp 145°-147° C.; nearly homogeneous by TLC in 95:5 $CH_2Cl_2$; mass spectrum (FAB) m/e 509, 511 (M+1)+. 200 MHz $^1$H NMR (CDCl$_3$) δ0.89 (t, J=7.1 Hz, 3H), 1.35 (m, 2H), 1.59 (m, 2H, partially obscured by H$_2$O peak), 2.58 (t, J=7.7 Hz, 2H), 4.04 (s, 2H), 5.51 (br s, 2H), 6.91 (dd, J≈8, 8 Hz, 1H), 7.25-7.32 (m, 2H), 7.66 (d, J=8.8 Hz, 1H), 8.25 (dd, J=8.8, 2.6 Hz, 1H), 8.41 (d, J=2.6 Hz, 1H).

Step F: 4-(4-Bromo-2-fluorobenzyl)-3-n-butyl-1-(2-chloro-5-nitrophenyl)-1H-pyrazole-5-carbonitrile A mixture of 600 mg (1.18 mmol) of 4-(4-bromo-2-fluorobenzyl)-3-n-butyl-1-(2-chloro-5-nitrophenyl)-1H-pyrazole-5-carboxamide (from Step E), 330 μL (238 mg, 2.35 mmol) of triethylamine, and 7 mL of methylene chloride was cooled to 0° C. and treated with 145 μL of trichloroacetyl chloride. The mixture was stirred under N$_2$ and allowed to warm to room temperature. After 3 hours, the mixture was concentrated to dryness. The orange residue was triturated with ether. The insoluble material was removed by filtration. The filtrate was washed with 0.2N HCl followed by 0.25N NaOH. The organic layer, after being dried over Na$_2$SO$_4$, was filtered and concentrated. The orange residual oil was flash chromatographed on silica gel (elution with 4:1 and then 3:1 hexane-EtOAc) to give 399 mg (69%) of the title compound as a yellow oil; nearly homogeneous by TLC in 3:1 hexane-EtOAc; mass spectrum (FAB) m/e 491, 493 (M+1)+. 200 MHz $^1$H NMR (CDCl$_3$) δ0.91 (t, J=7.1 Hz, 3H), 1.36 (m, 2H), 1.61 (m, 2H, partially obscured by H$_2$O peak), 2.61 (t, J=7.7 Hz, 2H), 3.97 (s, 2H), 7.07 (dd, J=8, 8 Hz, 1H), 7.26-7.31 (m, 2H), 7.78 (d, J=8.8 Hz, 1H), 8.31-8.39 (m, 2H).

Step G: 1-(5-Amino-2-chlorophenyl)-4-(4-bromo-2-fluorobenzyl)-3-n-butyl-1H-pyrazole-5-carbonitrile By the procedure of Example 1, Step I, 4-(4-bromo-2-fluorobenzyl)-3-n-butyl-1-(2-chloro-5-nitrophenyl)-1H-pyrazole-5-carbonitrile (from Step F) was hydrogenated in the presence of platinum oxide catalyst to give a 96% yield of the title compound as a tacky, orange oil; nearly homogeneous by TLC in 3:1 hexane-EtOAc; mass spectrum (FAB) m/e 461, 463 (M+1)+. 200 MHz $^1$H NMR (CDCl$_3$) δ0.89 (t, J=7.2 Hz, 3H), 1.33 (m, 2H), 1.58 (m, 2H), 2.58 (t, J=7.7 Hz, 2H), 3.94 (s, 2H), 6.69-6.75 (m, 2H), 7.03 (dd, J≈8, 8.5 Hz, 1H), 7.2-7.3 (m, 3H).

Step H: 4-(4-Bromo-2-fluorobenzyl)-3-n-butyl-1-[2-chloro-5-(propionylamino)phenyl]-1H-pyrazole-5-carbonitrile The acylation of 1-(5-amino-2-chlorophenyl)-4-(4-bromo-2-fluorobenzyl)-3-n-butyl-1H-pyrazole-5-carbonitrile (from Step G) with propionyl bromide in the presence of DMAP followed the procedure of Example 1, Step J. Flash chromatography of the crude product on silica gel (gradient elution with 5:1 to 3:1 hexane-EtOAc) afforded a 73% yield of the title compound as a tacky oil; homogeneous by TLC in 3:1 hexane-EtOAc; mass spectrum (FAB) m/e 517, 519 (M+1)+. 400 MHz $^1$H NMR (CDCl$_3$) δ0.87 (t, J=7.3 Hz, 3H), 1.22 (t, J=7.6 Hz, 3H), 1.32 (m, 2H), 1.54 (m, 2H, partially obscured by H$_2$O peak), 2.38 (q, J=7.6 Hz, 2H), 2.55 (t, J=7.8 Hz, 2H), 3.92 (s, 2H), 7.02 (dd, J≈8, 8.5

Hz, 1H), 7.22-7.26 (m, 2H), 7.4-7.5 (m, 2H), 7.90 (d, J=2.2 Hz, 1H).

Step I: 2-(N-t-Butylsulfamoyl)phenylboronic Acid

By the method described in Example 10, Step B, N-t-butylbenzenesulfonamide [G. Lombardino, J. Org. Chem., 36, 1843 (1971)] was deprotonated with n-butyllithium, and the resulting dianion was reacted with triisopropyl borate and worked up with acid to give the title compound, which was used directly in the next step without further purification.

Step J: 3-n-Butyl-4-[[2'-(N-t-butylsulfamoyl)-3-fluorobiphenyl-4-yl]methyl]-1-[2-chloro-5-(propionylamino)phenyl]-1H-pyrazole-5-carbonitrile A reaction flask was charged with 155 mg (0.299 mmol) of 4-(4-bromo-2-fluorobenzyl)-3-n-butyl-1-[2-chloro-5-(propionylamino)phenyl]-1H-pyrazole-5-carbonitrile (from Step H), 3.5 mL of toluene, 2.4 mL of ethanol, 615 μL (0.598 mmol) of a 250 mg/mL solution of 2-(N-t-butylsulfamoyl)phenylboronic acid (from Step I) in ethanol, 950 μL (1.20 mmol) of 1.25N NaOH, and 17 mg of tetrakis(triphenylphosphine)palladium(0). The mixture was stirred under $N_2$ at 90° C. for 5 hours, then cooled and concentrated. The residue was partitioned between 30 mL of ethyl acetate and 25 mL of $H_2O$. The organic layer was washed with brine, dried ($Na_2SO_4$), filtered, and evaporated in vacuo. The yellow residual oil was flash chromatographed on silica gel (elution with 3:1 and then 1:1 hexane-EtOAc) to give a 77% yield of the title compound as a slightly yellow, stiff foam; homogeneous by TLC in 3:1 hexane-EtOAc; mass spectrum (FAB) m/e 650 (M+1)+. 400 MHz $^1$H NMR (CDCl$_3$) δ0.92 (t, J=7.3 Hz, 3H), 100 (s, 9H), 1.21 (t, J=7.5 Hz, 3H), 1.38 (m, 2H), 1.65 (m, 2H), 2.39 (q, J=7.5 Hz, 2H), 2.66 (t, J=7.8 Hz, 2H), 3.98 (s, 1H), 4.02 (s, 2H), 7.2-7.6 (m, 8H), 7.82 (d, J=2.5 Hz, 1H), 8.15 (dd, J=7.9, 1.4 Hz, 1H).

Step K: 3-n-Butyl-1-[2-chloro-5-(propionylamino)phenyl]-4-[(3-fluoro-2'-sulfamoylbiphenyl-4-yl)methyl]-1H-pyrazole-5-carbonitrile A mixture of 142 mg (0.218 mmol) of 3-n-butyl-4-[[2'-(N-t-butylsulfamoyl)-3-fluorobiphenyl-4-yl]methyl]-1-[2-chloro-5-(propionylamino)phenyl]-1H-pyrazole-5-carbonitrile (from Step J), 237 μL (236 mg, 2.18 mmol) of anisole, and 675 μL of trifluoroacetic acid (TFA) was stirred at room temperature overnight in a stoppered flask. The mixture was evaporated under a stream of $N_2$, and the residue was flash chromatographed on silica gel (elution with 1% and then 3% MeOH in $CH_2Cl_2$), yielding 126 mg (97%) of the title compound as a slightly yellow, stiff foam; nearly homogeneous by TLC in 95:5 $CH_2Cl_2$—MeOH; mass spectrum (FAB) m/e 594 (M+1)+. 400 MHz $^1$H NMR (CDCl$_3$) δ0.93 (t, J=7.3 Hz, 3H), 1.20 (t, J=7.5 Hz, 3H), 1.40 (m, 2H), 1.67 (m, 2H), 2.37 (q, J=7.5 Hz, 2H), 2.69 (t, J=7.8 Hz, 2H), 4.02 (s, 2H), 4.52 (s, 2H), 7.2-7.6 (m, 8H), 7.81 (d, J=2.5 Hz, 1H), 8.15 (dd, J=8.0, 1.3 Hz, 1H).

Step L: 3-n-Butyl-4-[[2'-[N-(2-chlorobenzoyl)sulfamoyl]-3-fluorobiphenyl-4-yl]methyl]-1-[2-chloro-5-(propionylamino)phenyl]-1H-pyrazole-5-carbonitrile By the procedure of Example 1, Step H, 2-chlorobenzoic acid was converted to its imidazolide and reacted with 3-n-butyl-1-[2-chloro-5-(propionylamino)phenyl]-4-[[3-fluoro-2'-sulfamoylbiphenyl-4-yl]methyl]-1H-pyrazole-5-carbonitrile (from Step K). The crude product was purified by semipreparative HPLC on a Zorbax C8 reverse phase column (elution with 75:25 acetonitrile-$H_2O$ containing 0.1% TFA), affording a 74% yield of the title compound as a cream-colored, stiff foam; homogeneous by TLC in 95:5 $CH_2Cl_2$—MeOH; mass spectrum (FAB) m/e 732 (M+1)+. 400 MHz $^1$H NMR (CDCl$_3$) δ0.93 (t, J=7.3 Hz, 3H), 1.22 (t, J=7.5 Hz, 3H), 1.40 (m, 2H), 1.68 (m, 2H), 2.39 (q, J=7.5 Hz, 2H), 2.67 (t, J=7.8 Hz, 2H), 3.93 (br s, 2H), 7.1-7.7 (m, 12H), 7.77 (d, J=2.3 Hz, 1H), 8.37 (dd, J=7.9, 1.4 Hz, 1H), 9.10 (s, 1H).

EXAMPLE 5

3-n-Butyl-4-[[2'-[N-(2-chlorobenzoyl)sulfamoyl]-3-fluorobiphenyl-4-yl]methyl]-1-[2-chloro-5-(valerylamino)phenyl]-1H-pyrazole-5-carbonitrile This material was obtained by a route analogous to Example 4, except that valeryl chloride was substituted for propionyl bromide in Step H. The title compound was obtained as a solid, mp >95° C. (gradual); homogeneous by TLC in 95:5 $CH_2Cl_2$—MeOH; mass spectrum (FAB) m/e 760 (M+1)+. 400 MHz $^1$H NMR (CDCl$_3$) δ0.92 (m, 6H), 1.34-1.43 (m, 4H), 1.63-1.72 (m, 4H), 2.34 (t, J=7.5 Hz, 2H), 2.67 (t, J=7.8 Hz, 2H), 3.94 (br s, 2H), 7.09-7.67 (m, 12H), 7.79 (d, J=2.4 Hz, 1H), 8.37 (dd, J=7.9, 1.4 Hz, 1H), 9.10 (s, 1H).

Analysis ($C_{39}H_{36}Cl_2FN_5O_4S.0.5H_2O$): Calcd: C, 60.86; H, 4.85; N, 9.10. Found: C, 60.66; H, 4.74; N, 8.71.

EXAMPLE 6

4-[[2'-[N-(t-Butoxycarbonyl)sulfamoyl]-3-fluorobiphenyl-4-yl]methyl]-3-n-butyl-1-[2-chloro-5-(propionylamino)phenyl]-1H-pyrazole-5-carbonitrile A mixture of 40.9 mg (0.688 mmol) of 3-n-butyl-1-[2-chloro-5-(propionylamino)phenyl]-4-[(3-fluoro-2'-sulfamoylbiphenyl-4-yl)methyl]-1H-pyrazole-5-carbonitrile (from Example 4, Step K), 3.3 mg (0.826 mmol) of sodium hydride (60% in oil), and 1 mL of dry THF was stirred under $N_2$ at 60° C. for 4 hours. By this time, $H_2$ evolution was complete, and 30 mg (0.138 mmol) of di-t-butyl dicarbonate was added, and stirring under $N_2$ at 60° C. was continued overnight. The mixture was partitioned between ethyl acetate and $H_2O$ (to which a few drops of 2N HCl were added). The organic phase was washed with $H_2O$, dried ($Na_2SO_4$), and filtered. Concentration of the filtrate yielded an oil, which was first flash chromatographed on silica gel (gradient elution with 0.5-2% MeOH in $CH_2Cl_2$) and then further purified by semipreparative HPLC on a Zorbax C8 reverse phase column (elution with 80:20 acetonitrile-$H_2O$) to give 28.5 mg (58%) of the title compound as a slightly off-white, stiff foam, mp >95° C. (gradual); homogeneous by TLC in 95:5 $CH_2Cl_2$—MeOH; mass spectrum (FAB with Li spike) m/e 700 (M+Li)+. 400 MHz $^1$H NMR (CDCl$_3$) δ0.95 (t, J=7.3 Hz, 3H), 1.20 (t, J=7.5 Hz, 3H), 1.26 (s, 9H), 1.42 (m, 2H), 1.71 (m, 2H), 2.37 (q, J=7.5 Hz, 2H), 2.73 (t, J=7.7 Hz, 2H), 4.04 (br s, 2H), 7.07-7.15 (m, 2H), 7.27-7.36 (m, 2H), 7.42 (d, J=8.8 Hz, 1H), 7.52-7.64 (m, 4H), 7.72 (d, J=2.5 Hz, 1H), 8.24 (dd, J=8.0, 1.2 Hz, 1H).

Analysis ($C_{35}H_{37}ClFN_5O_5S.0.3CH_2Cl_2$): Calcd: C, 58.91; H, 5.27; N, 9.73. Found: C, 58.53; H, 5.16; N, 9.49.

EXAMPLE 7

4-[[2'-[N-(n-Butoxycarbonyl)sulfamoyl]-3-fluorobiphenyl-4-yl]methyl]-3-n-butyl-1-[2-chloro-5-(propionylamino)phenyl]-1H-pyrazole-5-carbonitrile This material was prepared by reaction of 3-n-butyl-1-[2-chloro-5-(propionylamino)phenyl]-4-[(3-fluoro-2'-sulfamoylbiphenyl-4-yl)methyl]-1H-pyrazole-5-carbonitrile (from Example 4, Step K) according to the method of Example 6, except that n-butyl chloroformate was substituted for di-t-butyl dicarbonate, and the overnight reaction was conducted at 50° C. The crude product was purified by reverse phase HPLC, as described in Example 6, to give a 30% yield of the title compound as a nearly white solid; homogeneous by TLC in 95:5 $CH_2Cl_2$—MeOH; mass spectrum (FAB) m/e 694 (M+1)+. 400 MHz $^1$H NMR (CDCl$_3$) δ0.81 (t, J=7.4 Hz, 3H), 0.95 (t, J=7.3 Hz, 3H), 1.15 (m, 2H), overlapping 1.21 (t, J=7.5 Hz, 3H), 1.38-1.46 (m, 2H), 1.72 (m, 2H), 2.38 (q, J=7.5 Hz, 2H), 2.74 (t, J=7.8 Hz, 2H), 3.97 (t, J=6.5 Hz, 2H), overlapping 4.04 (br s, 2H), 7.06-7.12 (m, 2H), 7.27-7.35 (m, 2H), 7.40-7.68 (m, 5H), 7.97 (s, 1H), 8.26 (dd, J=8.0, 1.3 Hz, 1H).

Analysis ($C_{35}H_{37}ClFN_5O_5S.0.7CH_2Cl_2$): Calcd: C, 57.00; H, 4.96; N, 9.30. Found: C, 57.10; H, 4.69; N, 8.94.

EXAMPLE 8

3-n-Butyl-1-[5-(N-n-butylcarbamoyl)-2-(trifluoromethyl)phenyl]-4-[[2'-[N-(2-chlorobenzoyl)sulfamoyl]-3-fluorobiphenyl-4-yl]methyl]-1H-pyrazole-5-carbonitrile Step A: 2-Nitro-4-methylbenzotrifluoride A mixture of 6.00 g (27.8 mmol) of 4-bromo-3-nitrotoluene, 5.86 mL (8.03 g, 55.6 mmol) of methyl chlorodifluoroacetate, 1.93 g (33.4 mmol) of potassium fluoride, 5.31 g (27.8 mmol) of cuprous iodide, and 25 mL of dry DMF was stirred at 110° C. for 2 days. The cooled material was diluted with aqueous citric acid and extracted 3× with ethyl acetate. The combined organic extracts were washed with H$_2$O, then with brine, and dried over anhydrous Na$_2$SO$_4$. The residue obtained upon concentration of the filtered solution was flash chromatographed 3× on silica gel (elution with 100:1 and 25:1 hexane-EtOAc) to give 3.25 g (57%) of the title compound as a yellow liquid; homogeneous by TLC in 4:1 hexane-EtOAc; mass spectrum (EI) m/e 205 (M+). 400 MHz $^1$H NMR (CDCl$_3$) δ2.48 (s, 3H), 7.49 (d, J=8 Hz, 1H), 7.67 (s, 1H) overlapping 7.68 (d, J=8 Hz, 1H).

Step B: 3-Nitro-4-(trifluoromethyl)benzoic acid

To a rapidly stirred mixture of 1.00 g (4.88 mmol) of 2-nitro-4-methylbenzotrifluoride (from Step A), 236 mg (0.732 mmol) of tetra-n-butylammonium bromide, 51 mg (0.244 mmol) of ruthenium trichloride hydrate, and 2 mL of 1,2-dichloroethane were added five 5.8 -mL (approximately 22 mmol) portions of 13% sodium hypochlorite solution (aqueous, approx. 3.8M) while monitoring and adjusting the pH. With each addition of sodium hypochlorite solution, 5N NaOH was added as necessary to maintain the pH between 8.5 and 10.5, and the next portion of sodium hypochlorite was added only when the pH was stable for about 5 minutes. The entire addition required approximately 2 hours, and the final pH was 10.3. After being stirred overnight at 45° C., the 2-phase mixture was cooled and separated. The aqueous phase was acidified to pH 3 by addition of 20% sulfuric acid and extracted 3× with ethyl acetate. The combined organic extracts were washed with H$_2$O (3×), then with brine, and dried over anhydrous Na$_2$SO$_4$. The residue obtained upon concentration was taken up in 5% NaHCO$_3$ (aqueous) adjusted to pH 9 with 5% NaOH. The aqueous phase was washed twice with methylene chloride and then with ether. Next, the water phase was acidified with 20% sulfuric acid and extracted with ethyl acetate as above to yield 563 mg (49%) of the title compound as an off-white solid, mp 156°-158° C.; TLC in 1:1 hexane-EtOAc (at origin); mass spectrum (EI) m/e 235 (M+). 200 MHz $^1$H NMR (CD$_3$OD) δ7.87 (d, J=8 Hz, 1H), 8.31 (d, J=8 Hz, 1H), 8.45 (s, 1H).

Step C: Ethyl 3-Nitro-4-(trifluoromethyl)benzoate

A solution of 555 mg (2.36 mmol) of 3-nitro-4-(trifluoromethyl)benzoic acid (from Step B) in 10 mL of ethanol was treated with 1 mL of concentrated hydrochloric acid. The solution was stirred at reflux for 2 days, then cooled, and partitioned between ethyl acetate and H$_2$O. The organic layer was washed successively with saturated NaHCO$_3$, H$_2$O, and brine. The ethyl acetate solution was then dried over Na$_2$SO$_4$ and concentrated to give 400 mg (64%) of the title compound as a pale yellow foam, homogeneous by TLC in 4:1 hexane-EtOAc; mass spectrum (EI) m/e 263 (M+). 200 MHz $^1$H NMR (CDCl$_3$) δ1.43 (t, J=7.2 Hz, 3H), 4.46 (q, J=7.2 Hz, 2H), 7.92 (d, J=8 Hz, 1H), 8.36 (d, J=8 Hz, 1H), 8.49 (s, 1H).

Step D: Ethyl 3-Amino-4-(trifluoromethyl)benzoate

A mixture of 395 mg (1.50 mmol) of ethyl 3-nitro-4-(trifluoromethyl)benzoate (from Step C), 20 mg of platinum oxide, and 6 mL of ethanol was shaken with hydrogen at 3-4 atm. for a few hours, by which time the reaction was essentially complete. The catalyst was removed by filtration, and the filtrate was concentrated to dryness. The residue was chromatographed on silica gel (elution with 25:1 hexane-EtOAc) to afford a 77% yield of the title compound as a pale yellow, gummy foam; TLC in 4:1 hexane-EtOAc; mass spectrum (EI) m/e 233 (M+). 200 MHz $^1$H NMR (CD$_3$OD) δ1.36 (t, J=7.1 Hz, 3H), 4.33 (q, J=7.1 Hz, 2H), 7.26 (d, J=8 Hz, 1H), 7.44 (d, J=8 Hz, 1H) overlapping 7.47 (s, 1H).

Step E: Ethyl 3-Hydrazino-4-(trifluoromethyl)benzoate hydrochloride

A mixture of 500 mg (2.15 mmol) of ethyl 3-amino-4-(trifluoromethyl)benzoate (from Step D) and 5 mL of concentrated hydrochloric acid was stirred at 0°-5° C. as a cold solution of 173 mg (2.50 mmol) of sodium nitrite in 0.8 mL of H$_2$O was added. After being stirred at 0°-5° C. for 1 hour, the mixture was filtered while cold, and the filtrate was poured into a solution of 1.02 g (4.5 mmol) of stannous chloride dihydrate in 2 mL of concentrated hydrochloric acid stirred at 0° C. Precipitation occurred immediately. The mixture was kept in an ice bath for 1.5 hours, and then the solid was collected by filtration. The solid is dried to yield the title compound suitable for use in the pyrazole ring formation reaction. In this experiment, the material was characterized as the free base by partitioning the solid hydrochloride between 2N Na$_2$CO$_3$ (aqueous) and ethyl acetate. The ethyl acetate phase was washed with brine, dried, filtered, and concentrated to yield 375 mg (70%) of the free base of the title compound as a pale yellow oil; homogeneous by TLC in 4:1 hexane-EtOAc and 98:2 CH$_2$Cl$_2$—MeOH. 200 MHz $^1$H NMR (CD$_3$OD) for free base: δ1.38 (t, J=7.1 Hz, 3H), 4.36 (q, J=7.1 Hz, 2H), 7.34 (d, J=8 Hz, 1H), 7.48 (d, J=8 Hz, 1H), 8.05 (s, 1H).

Step F: 3-(4-Bromo-2-fluorobenzyl)-2-methoxyimino-4-oxooctanoic Acid

This material is prepared by saponification of ethyl 3-(4-bromo-2-fluorobenzyl)-2-methoxyimino-4-oxooctanoate (from Example 4, Step A) using the method of Example 2.

Step G: 3-(4-Bromo-2-fluorobenzyl)-2-methoxyimino-4-oxooctanoyl Chloride

The title compound is prepared by reaction of 3-(4-bromo-2-fluorobenzyl)-2-methoxyimino-4-oxooctanoic acid (from Step F) with thionyl chloride according to the procedure of Example 4, Step D. The material is used without purification in the next step.

Step H: 3-(4-Bromo-2-fluorobenzyl)-2-methoxyimino-4-oxooctanamide

The title compound is prepared from 3-(4-bromo-2-fluorobenzyl)-2-methoxyimino-4-oxooctanoyl chloride (from Step G) according to the method of Example 4, Step E, except that instead of bubbling ammonia into the cold reaction mixture, it is preferable to prepare a saturated solution of ammonia in THF (at about −50° C.) and add this cold solution gradually (under protection from moisture) to a stirred solution of the acid chloride in THF at −50° C.

Step I: 3-(4-Bromo-2-fluorobenzyl)-2-methoxyimino-4-oxooctanenitrile

The title compound is prepared by reaction of 3-(4-bromo-2-fluorobenzyl)-2-methoxyimino-4-oxooctanamide (from Step H) with trichloroacetyl chloride in the presence of triethylamine according to the procedure of Example 4, Step F. Alternatively, the following procedure is used. To 1 mmol of the amide from Step H is added about 12 mL of polyphosphate ester (PPE) [M. Cava, M. Lakshmikantham, and M. Mitchell, J. Org. Chem., 34, 2665 (1969)] solution, consisting of approximately a 2:1 ratio of PPE and CDCl$_3$ (used as a surrogate for alcohol-free chloroform). The mixture is stirred at reflux under N$_2$ for about 3 hours, and then the solvent is removed by concentration in vacuo. The residue is cooled in an ice bath and treated with an excess of saturated aqueous Na$_2$CO$_3$. The mixture is stirred for 1 hour and then extracted with ethyl acetate. The organic phase is washed further with H$_2$O, then dried over Na$_2$SO$_4$, filtered, and concentrated. The residue is purified by column chromatography on silica gel (elution with hexane-EtOAc) to afford the title compound.

Step J: 3-[[2'-(N-t-Butylsulfamoyl)-3-fluorobiphenyl-4-yl]methyl]-b 2-methoxyimino-4-oxooctanenitrile By the procedure of Example 4, Step J, 3-(4-bromo-2-fluorobenzyl)-2-methoxyimino-4-oxooctanenitrile (from Step I) is coupled with 2-(N-t-butylsulfamoyl)-phenylboronic acid (from Example 4, Step I) in the presence of catalytic tetrakis(triphenylphosphine)palladium(0) to yield the title compound.

Step K: 3-n-Butyl-1-[5-(ethoxycarbonyl)-2-(trifluoromethyl)phenyl]-4-[(3-fluoro-2'-sulfamoylbiphenyl-4-yl)methyl]-1H-pyrazole-5-carbonitrile The title compound is prepared by reaction of 3-[[2'-(N-t-butylsulfamoyl)-3-fluorobiphenyl-4-yl]methyl]-2-methoxyimino-4-oxooctanenitrile (from Step J) with ethyl 3-hydrazino-4-(trifluoromethyl)benzoate hydrochloride (from Step E) according to the procedure of Example 1, Step G.

Step L: 3-n-Butyl-1-[5-(N-n-butylcarbamoyl)-2-(trifluoromethyl)phenyl]-4-[(3-fluoro-2'-sulfamoylbiphenyl-4-yl)methyl]-1H-pyrazole-5-carbonitrile A solution of 3-n-butyl-1-[5-(ethoxycarbonyl)-2-(trifluoromethyl)phenyl]-4-[(3-fluoro-2'-sulfamoylbiphenyl-4-yl)methyl]-1H-pyrazole-5-carbonitrile (from Step K) in n-butylamine (approximately 10 mL of amine per mmole of ester) is heated in a sealed tube at 120° C. overnight. Volatiles are removed by evaporation, and the residue is chromatographed on silica gel (elution with CH$_2$Cl$_2$—MeOH) to provide the title compound.

Step M: 3-n-Butyl-1-[5-(N-n-butylcarbamoyl)-2-(trifluoromethyl)phenyl]-4-[[2'-[N-(2-chlorobenzoyl)sulfamoyl]-3-fluorobiphenyl-4-yl]methyl]-1H-pyrazole-5-carbonitrile Following the procedure of Example 1, Step H, 2-chlorobenzoic acid is converted to its imidazolide with CDI and subsequently reacted with 3-n-butyl-1-[5-(N-n-butylcarbamoyl)-2-(trifluoromethyl)phenyl]-4-[(3-fluoro-2'-sulfamoylbiphenyl-4-yl)methyl]-1H-pyrazole-5-carbonitrile (from Step L) in the presence of DBU to yield the title compound.

EXAMPLE 9

3-n-Butyl-4-[[2'-[N-(2-chlorobenzoyl)sulfamoyl]-3-fluorobiphenyl-4-yl]methyl]-1-[5-[(2-methoxyacetyl)amino]-2-(trifluoromethyl)phenyl]-1H-pyrazole-5-carbonitrile Step A: 1-(2-Bromo-5-nitrophenyl)-3-n-butyl-4-[(3-fluoro-2'-sulfamoylbiphenyl-4-yl)methyl]-1H-pyrazole-5-carbonitrile The title compound is prepared by reaction of 3-[[2'-(N-t-butylsulfamoyl)-3-fluorobiphenyl-4-yl]methyl]-2-methoxyimino-4-oxooctanenitrile (from Example 8, Step J) with 2-bromo-5-nitrophenylhydrazine hydrochloride [prepared from 2-bromo-5-nitroaniline according to H. Stroh and G. Westphal, Chem. Ber., 96, 184 (1963)], following the procedure of Example 1, Step G.

Step B: 3-n-Butyl-4-[(3-fluoro-2'-sulfamoylbiphenyl-4-yl)methyl]-1-[5-nitro-2-(trifluoromethyl)phenyl]-1H-pyrazole-5-carbonitrile A mixture of 1-(2-bromo-5-nitrophenyl)-3-n-butyl-4-[(3-fluoro-2'-sulfamoylbiphenyl-4-yl)methyl]-1H-pyrazole-5-carbonitrile (from Step A) (1 equivalent), methyl chlorodifluoroacetate (2 equiv), potassium fluoride (1 equiv), cuprous iodide (1 equiv), potassium bromide (1 equiv), and DMF (approximately 3 mL per gram of pyrazole compound) is stirred under N$_2$ in a sealed tube at 120° C. for about 15 hours. The cooled mixture is diluted with H$_2$O and extracted a few times with ethyl acetate. The combined organic fractions are washed with brine, dried over Na$_2$SO$_4$, and filtered. The filtrate is concentrated, and the residue is chromatographed on silica gel (elution with CH$_2$Cl$_2$—MeOH) to yield the title compound.

Step C: 3-n-Butyl-4-[[2'-[N-(2-chlorobenzoyl)sulfamoyl]-3-fluorobiphenyl-4-yl]methyl]-1-[5-nitro-2-(trifluoromethyl)phenyl]-1H-pyrazole-5-carbonitrile By the method of Example 1, Step H, 2-chlorobenzoic acid is converted to its imidazolide and reacted with 3-n-butyl-4-[(3-fluoro-2'-sulfamoylbiphenyl-4-yl)methyl]-1-[5-nitro-2-(trifluoromethyl)phenyl]-1H-pyrazole-5-carbonitrile (from Step B) in the presence of DBU to give the title compound.

Step D: 1-[5-Amino-2-(trifluoromethyl)phenyl]-3-n-butyl-4-[[2'-[N-(2-chlorobenzoyl)sulfamoyl]-3-fluorobiphenyl-4-yl]methyl]-1H-pyrazole-5-carbonitrile The title compound is prepared by hydrogenation of 3-n-butyl-4-[[2'-[N-(2-chlorobenzoyl)sulfamoyl]-3-fluorobiphenyl-4-yl]methyl]-1-[5-nitro-2-(trifluoromethyl)phenyl]-1H-pyrazole-5-carbonitrile (from Step C) according to the procedure of Example 1, Step I.

Step E: 3-n-Butyl-4-[[2'-[N-(2-chlorobenzoyl)sulfamoyl]-3-fluorobiphenyl-4-yl]methyl]-1-[5-[(2-methoxyacetyl)amino]-2-(trifluoromethyl)phenyl]-1H-pyrazole-5-carbonitrile The title compound is obtained by reaction of 1-[5-amino-2-(trifluoromethyl)phenyl]-3-n-butyl-4-[[2'-[N-(2-chlorobenzoyl)sulfamoyl]-3-fluorobiphenyl-4-yl]methyl]-1H-pyrazole-5-carbonitrile (from Step D) with methoxyacetyl chloride in the presence of DMAP in pyridine according to the procedure of Example 1, Step J.

EXAMPLE 10

1-[5-(Acetylamino)-2-chlorophenyl]-3-n-butyl-4-[[3-fluoro-2'-[N-(2-fluorobenzoyl)sulfamoyl]-5'-n-propyl-biphenyl-4-yl]methyl]-1H-pyrazole-5-carbonitrile Step A: N-t-Butyl-4-n-propylbenzenesulfonamide To a solution of 4-n-propylbenzenesulfonyl chloride (Lancaster) in anhydrous $CH_2Cl_2$ (0.5M solution) cooled to 0° C. under $N_2$ was added t-butylamine (2.2 equivalents) slowly through a dropping funnel. After complete addition, the reaction was stirred at room temperature for 12 hours. The $CH_2Cl_2$ was removed under reduced pressure, and the residue was extracted into ether and washed with 2N NaOH, $H_2O$ and brine. The organic phase was dried over anhydrous $MgSO_4$ and concentrated in vacuo to afford the title compound; TLC in 3:1 hexane-EtOAc ($R_f=0.46$) (3:1 hexane-EtOAc). 200 MHz $^1H$ NMR ($CDCl_3$) δ0.93 (t, 3H), 1.22 (s, 9H), 1.62 (m, 2H), 2.65 (t, 2H), 4.67 (br s, 1H), 7.27 (d, 2H), 7.79 (d, 2H).

Step B: 2-(N-t-Butylsulfamoyl)-5-n-propylphenylboronic acid

To a solution of 2.85 g (11.2 mmol) of N-t-butyl-4-n-propylbenzenesulfonamide (from Step A) in anhydrous THF (20 mL) cooled to −40° C. under $N_2$ was added 2.5M n-butyllithium solution (11.2 mL, 2.5 equiv). The mixture was warmed to room temperature and stirred for 2 hours. To the mixture, containing the bright red dianion at 0° C., was added triisopropyl borate (3.9 mL, 1.5 equivalents). The next day, 2N HCl (3 mL) was added and the mixture was stirred for 1 hour. The solvent was removed under reduced pressure and the residue was extracted with ethyl acetate. The organic solution was washed with 2N HCl, $H_2O$ and brine. The organic phase was dried over anhydrous $MgSO_4$ and concentrated in vacuo to afford 3.34 g (100%) of the title compound; TLC in 1:1 EtOAc-hexane ($R_f=0.5$). The material is used in the next step without further purification.

Step C: 3-[[2'-(N-t-Butylsulfamoyl)-3-fluoro-5'-n-propylbiphenyl-4-yl]methyl]-2-methoxyimino-4-oxooctanenitrile By the procedure of Example 4, Step J, 2-(N-t-butyl-sulfamoyl)phenylboronic acid (from Step B) is coupled with 3-(4-bromo-2-fluorobenzyl)-2-methoxyimino-4-oxooctanenitrile (from Example 8, Step I) in the presence of catalytic tetrakis(triphenylphosphine)palladium(0) to yield the title compound.

Step D: 3-n-Butyl-1-(2-chloro-5-nitrophenyl)-4-[(3-fluoro-5'-n-propyl-2'-sulfamoylbiphenyl-4-yl)methyl]-1H-pyrazole-5-carbonitrile The reaction of 3-[[2'-(N-t-butylsulfamoyl)-3-fluoro-5'-n-propylbiphenyl-4-yl]methyl]-2-methoxyimino-4-oxooctanenitrile (from Step C) with 2-chloro-5-nitrophenylhydrazine hydrochloride according to the procedure of Example 1, Step G, yields the title compound.

Step E: 3-n-Butyl-1-(2-chloro-5-nitrophenyl)-4-[[3-fluoro-2'-[N-(2-fluorobenzoyl)sulfamoyl]-5'-n-propyl-biphenyl-4-yl]methyl]-1H-pyrazole-5-carbonitrile By the method of Example 1, Step H, 2-fluorobenzoic acid is converted to its imidazolide and reacted with 3-n-butyl-1-(2-chloro-5-nitrophenyl)-4-[(3-fluoro-5'-n-propyl-2'-sulfamoylbiphenyl-4-yl)methyl]-1H-pyrazole-5-carbonitrile (from Step D) in the presence of DBU to give the title compound.

Step F: 1-(5-Amino-2-chlorophenyl)-3-n-butyl-4-[[3-fluoro-2'-[N-(2-fluorobenzoyl)sulfamoyl]-5'-n-propyl-biphenyl-4-yl]methyl]-1H-pyrazole-5-carbonitrile The hydrogenation of 3-n-butyl-1-(2-chloro-5-nitrophenyl)-4-[[3-fluoro-2'-[N-2-fluorobenzoyl)sulfamoyl]-5'-n-propylbiphenyl-4-yl]methyl]-1H-pyrazole-5-carbonitrile (from Step E) according to the procedure of Example 1, Step I, provides the title compound.

Step G: 1-[5-(Acetylamino)-2-chlorophenyl]-3-n-butyl-4-[[3-fluoro-2'-[N-(2-fluorobenzoyl)sulfamoyl]-5'-n-propylbiphenyl-4-yl]methyl]-1H-pyrazole-5-carbonitrile The title compound is obtained by reaction of 1-(5-amino-2-chlorophenyl)-3-n-butyl-4-[[3-fluoro-2'-[N-(2-fluorobenzoyl)sulfamoyl]-5'-n-propylbiphenyl-4-yl]methyl]-1H-pyrazole-5-carbonitrile (from Step F) with acetyl chloride in the presence of DMAP in pyridine according to the method of Example 1, Step J.

The following representative compounds of formula (I) can be prepared using the procedures of the foregoing Examples and Reaction Schemes:

(1) 3-n-butyl-4-[[2'-[N-(2-chlorobenzoyl)sulfamoyl]-3-fluorobiphenyl-4-yl]methyl]-1-[5-(propionylamino)-2-(trifluoromethyl)phenyl]-1H-pyrazole-5-carbonitrile;

(2) 3-n-butyl-4-[[3-fluoro-2'-[N-(2-fluorobenzoyl)sulfamoyl]biphenyl-4-yl]methyl]-1-[5-(propionylamino)-2-(trifluoromethyl)phenyl]-1H-pyrazole-5-carbonitrile;

(3) 3-n-butyl-4-[[2'-[N-(2,5-difluorobenzoyl)sulfamoyl]-3-fluorobiphenyl-4-yl]methyl]-1-[5-(propionylamino)-2-(trifluoromethyl)phenyl]-1H-pyrazole-5-carbonitrile;

(4) 3-n-butyl-4-[[2'-[N-(2-chlorobenzoyl)sulfamoyl]-3-fluorobiphenyl-4-yl]methyl]-1-[2-chloro-5-[(2-methoxyacetyl)amino]phenyl]-1H-pyrazole-5-carbonitrile;

(5) 3-n-butyl-4-[[2'-[N-(2-chlorobenzoyl)sulfamoyl]-3-fluorobiphenyl-4-yl]methyl]-1-[5-[(2-methoxyacetyl)amino]-2-(trifluoromethyl)phenyl]-1H-pyrazole-5-carbonitrile;

(6) 3-n-butyl-4-[[2'-[N-(2-chlorobenzoyl)sulfamoyl]-3-fluorobiphenyl-4-yl]methyl]-1-[2-chloro-5-[(2-ethoxyacetyl)amino]phenyl]-1H-pyrazole-5-carbonitrile;

(7) 3-n-butyl-4-[[2'-[N-(2-chlorobenzoyl)sulfamoyl]-3-fluorobiphenyl-4-yl]methyl]-1-[5-[(2-ethoxyacetyl)amino]-2-(trifluoromethyl)phenyl]-1H-pyrazole-5-carbonitrile;

(8) 3-n-butyl-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carbonitrile;

(9) 3-n-butyl-4-[[3-fluoro-2'-[N-(2-fluorobenzoyl)sulfamoyl]biphenyl-4-yl]methyl]-1-[5-[(2-ethoxyacetyl)amino]-2-(trifluoromethyl)phenyl]-1H-pyrazole-5-carbonitrile;

(10) 3-n-butyl-1-[5-(N-n-butylcarbamoyl)-2-chlorophenyl]-4-[[2'-[N-(2-chlorobenzoyl)sulfamoyl]-3-fluorobiphenyl-4-yl]methyl]-1H-pyrazole-5-carbonitrile;

(11) 3-n-butyl-1-[5-(N-n-butylcarbamoyl)-2-(trifluoromethyl)phenyl]-4-[[2'-[N-(2-chlorobenzoyl)sulfamoyl]-3-fluorobiphenyl-4-yl]methyl]-1H-pyrazole-5-carbonitrile;

(12) 3-n-butyl-1-[5-(N-n-butylcarbamoyl)-2-(trifluoromethyl)phenyl]-4-[[3-fluoro-2'-[N-(2- fluorobenzoyl)sulfamoyl]biphenyl-4-yl]methyl]-1H-pyrazole-5-carbonitrile;

(13) 3-n-butyl-1-[5-(N-n-butylcarbamoyl)-2-(trifluoromethyl)phenyl]-4-[[2'-[N-(2,5-difluorobenzoyl)sulfamoyl]-3-fluorobiphenyl-4-yl]methyl]-1H-pyrazole-5-carbonitrile;

(14) 3-n-butyl-4-[[2'-[N-(2-chlorobenzoyl)sulfamoyl]-3-fluorobiphenyl-4-yl]methyl]-1-[5-(N-n-propylcarbamoyl)-2-(trifluoromethyl)phenyl]-1H-pyrazole-5-carbonitrile;

(15) 3-n-butyl-4-[[3-fluoro-2'-[N-(2-fluorobenzoyl)sulfamoyl]biphenyl-4-yl]methyl]-1-[5-(N-n-propylcarbamoyl)-2-(trifluoromethyl)phenyl]-1H-pyrazole-5-carbonitrile;

(16) 3-n-butyl-1-[5-(butyrylamino)-2-chlorophenyl]-4-[[2'-[N-(2-chlorobenzoyl)sulfamoyl]-3-fluorobiphenyl-4-yl]methyl]-1H-pyrazole-5-carbonitrile;

(17) 1-[2-bromo-5-(propionylamino)phenyl]-3-n-butyl-4-[[3-fluoro-2'-[N-(2-fluorobenzoyl)sulfamoyl]biphenyl-4-yl]methyl]-1H-pyrazole-5-carbonitrile;

(18) 1-[2-bromo-5-[2-(methoxyacetyl)amino]phenyl]-3-n-butyl-4-[[3-fluoro-2'-[N-(2-fluorobenzoyl)sulfamoyl]biphenyl-4-yl]methyl]-1H-pyrazole-5-carbonitrile;

(19) 1-[2-bromo-5-[2-(ethoxyacetyl)amino]phenyl]-3-n-butyl-4-[[3-fluoro-2'-[N-(2-fluorobenzoyl)sulfamoyl]biphenyl-4-yl]methyl]-1H-pyrazole-5-carbonitrile;

(20) 1-[2-bromo-5-(N-n-butylcarbamoyl)phenyl]-3-n-butyl-4-[[3-fluoro-2'-[N-(2-fluorobenzoyl)sulfamoyl]biphenyl-4-yl]methyl]-1H-pyrazole-5-carbonitrile;

(21) 3-n-butyl-4-[[2'-[N-(2-chlorobenzoyl)sulfamoyl]-3-fluorobiphenyl-4-yl]methyl]-1-[2-chloro-5-[(n-propoxycarbonyl)amino]phenyl]-1H-pyrazole-5-carbonitrile;

(22) 3-n-butyl-4-[[2'-[N-(2-chlorobenzoyl)sulfamoyl]-3-fluorobiphenyl-4-yl]methyl]-1-[2-chloro-5-[(n-propylaminocarbonyl)amino]phenyl]-1H-pyrazole-5-carbonitrile;

(23) 3-n-butyl-4-[[2'-[N-(2-chlorobenzoyl)sulfamoyl]-3-fluorobiphenyl-4-yl]methyl]-1-[2-chloro-5-[(morpholinocarbonyl)amino]phenyl]-1H-pyrazole-5-carbonitrile;

(24) 3-n-butyl-1-[5-(N-n-butyl-N-methylcarbamoyl)-2-chlorophenyl]-4-[[2'-[N-(2-chlorobenzoyl)sulfamoyl]-3-fluorobiphenyl-4-yl]methyl]-1H-pyrazole-5-carbonitrile;

(25) 3-n-butyl-4-[[2'-[N-(2-chlorobenzoyl)sulfamoyl]-3-fluorobiphenyl-4-yl]methyl]-1-[2-chloro-5-(morpholinocarbonyl)phenyl]-1H-pyrazole-5-carbonitrile;

(26) 3-n-butyl-1-(2-chloro-5-valerylphenyl)-4-[[2'-[N-(2-chlorobenzoyl)sulfamoyl]-3-fluorobiphenyl-4-yl]methyl]-1H-pyrazole-5-carbonitrile;

(27) 3-n-butyl-1-(2-chloro-5-valerylphenyl)-4-[[3-fluoro-2'-[N-(2-fluorobenzoyl)sulfamoyl]biphenyl-4-yl]methyl]-1H-pyrazole-5-carbonitrile;

(28) 3-n-butyl-4-[[3-fluoro-2'-[N-(2-fluorobenzoyl)sulfamoyl]biphenyl-4-yl]methyl]-1-[2-(trifluoromethyl)-5-valerylphenyl]-1H-pyrazole-5-carbonitrile;

(29) 1-[5-(benzoylamino)-2-(trifluoromethyl)phenyl]-3-n-butyl-4-[[2'-[N-(2-chlorobenzoyl)sulfamoyl]-3-fluorobiphenyl-4-yl]methyl]-1H-pyrazole-5-carbonitrile;

(30) 3-n-butyl-4-[[2'-[N-(2-chlorobenzoyl)sulfamoyl]-3-fluorobiphenyl-4-yl]methyl]-1-[5-(isonicotinoylamino)-2-(trifluoromethyl)phenyl]-1H-pyrazole-5-carbonitrile;

(31) 3-n-butyl-1-[5-(n-butylsulfinyl)-2-chlorophenyl]-4-[[2'-[N-(2-chlorobenzoyl)sulfamoyl]-3-fluorobiphenyl-4-yl]methyl]-1H-pyrazole-5-carbonitrile;

(32) 3-n-butyl-1-[5-(n-butylsulfinyl)-2-(trifluoromethyl)phenyl]-4-[[2'-[N-(2-chlorobenzoyl)sulfamoyl]-3-fluorobiphenyl-4-yl]methyl]-1H-pyrazole-5-carbonitrile;

(33) 3-n-butyl-1-[5-(n-butylsulfinyl)-2-(trifluoromethyl)phenyl]-4-[[3-fluoro-2'-[N-(2-fluorobenzoyl)sulfamoyl]biphenyl-4-yl]methyl]-1H-pyrazole-5-carbonitrile;

(34) 3-n-butyl-4-[[3-fluoro-2'-[N-(2-fluorobenzoyl)sulfamoyl]biphenyl-4-yl]methyl]-1-[5-[(1-propanesulfonyl)amino]-2-(trifluoromethyl)phenyl]-1H-pyrazole-5-carbonitrile;

(35) 3-n-butyl-1-[5-(N-n-butylsulfamoyl)-2-(trifluoromethyl)phenyl]-4-[[2'-[N-(2-chlorobenzoyl)sulfamoyl]-3-fluorobiphenyl-4-yl]methyl]-1H-pyrazole-5-carbonitrile;

(36) 4-[[2'-[N-(2-chlorobenzoyl)sulfamoyl]-3-fluorobiphenyl-4-yl]methyl]-1-[2-chloro-5-(propionylamino)phenyl]-3-n-propyl-1H-pyrazole-5-carbonitrile;

(37) 4-[[2'-[N-(2-chlorobenzoyl)sulfamoyl]-3-fluorobiphenyl-4-yl]methyl]-1-[5-(propionylamino)-2-(trifluoromethyl)phenyl]-3-n-propyl-1H-pyrazole-5-carbonitrile;

(38) 4-[[3-fluoro-2'-[N-(2-fluorobenzoyl)sulfamoyl]biphenyl-4-yl]methyl]-1-[5-(propionylamino)-2-(trifluoromethyl)phenyl]-3-n-propyl-1H-pyrazole-5-carbonitrile;

(39) 4-[[3-fluoro-2'-[N-(2-fluorobenzoyl)sulfamoyl]biphenyl-4-yl]methyl]-1-[5-[(methoxyacetyl)amino]-2-(trifluoromethyl)phenyl]-3-n-propyl-1H-pyrazole-5-carbonitrile;

(40) 1-[5-[(ethoxyacetyl)amino]-2-(trifluoromethyl)phenyl]-4-[[3-fluoro-2'-[N-(2-fluorobenzoyl)sulfamoyl]biphenyl-4-yl]methyl]-3-n-propyl-1H-pyrazole-5-carbonitrile;

(41) 1-[5-(N-n-butylcarbamoyl)-2-chlorophenyl]-4-[[2'-[N-(2-chlorobenzoyl)sulfamoyl]-3-fluorobiphenyl-4-yl]methyl]-3-n-propyl-1H-pyrazole-5-carbonitrile;

(42) 1-[5-(N-n-butylcarbamoyl)-2-chlorophenyl]-4-[[3-fluoro-2'-[N-(2-fluorobenzoyl)sulfamoyl]biphenyl-4-yl]methyl]-3-n-propyl-1H-pyrazole-5-carbonitrile;

(43) 1-[5-(N-n-butylcarbamoyl)-2-(trifluoromethyl)phenyl]-4-[[2'-[N-(2-chlorobenzoyl)sulfamoyl]-3-fluorobiphenyl-4-yl]methyl]-3-n-propyl-1H-pyrazole-5-carbonitrile;

(44) 1-[5-(N-n-butylcarbamoyl)-2-(trifluoromethyl)phenyl]-4-[[3-fluoro-2'-[N-(2-fluorobenzoyl)sulfamoyl]biphenyl-4-yl]methyl]-3-n-propyl-1H-pyrazole-5-carbonitrile;

(45) 3-n-butyl-4-[[3-chloro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carbonitrile;

(46) 3-n-butyl-1-[5-(N-n-butylcarbamoyl)-2-(trifluoromethyl)phenyl]-4-[[3-chloro-2'-[N-(2-fluorobenzoyl)sulfamoyl]biphenyl-4-yl]methyl]-1H-pyrazole-5-carbonitrile;

(47) 1-[5-(acetylamino)-2-chlorophenyl]-3-n-butyl-4-[[2'-[N-(2-fluorobenzoyl)sulfamoyl]-5'-n-propylbiphenyl-4-yl]methyl]-1H-pyrazole-5-carbonitrile;

(48) 1-[5-(acetylamino)-2-chlorophenyl]-3-n-butyl-4-[[3-fluoro-2'-[N-(2-fluorobenzoyl)sulfamoyl]-5'-n-propylbiphenyl-4-yl]methyl]-1H-pyrazole-5-carbonitrile;

(49) 1-[5-(acetylamino)-2-chlorophenyl]-3-n-butyl-4-[[3-fluoro-2'-[N-(ethoxycarbonyl)sulfamoyl]-5'-n-propylbiphenyl-4-yl]methyl]-1H-pyrazole-5-carbonitrile;

(50) 1-[5-(acetylamino)-2-chlorophenyl]-4-[[3-fluoro-2'-[N-(2-fluorobenzoyl)sulfamoyl]-5'-n-propylbiphenyl-4-yl]methyl]-3-n-propyl-1H-pyrazole-5-carbonitrile;

(51) 1-[5-(acetylamino)-2-chlorophenyl]-4-[[3-fluoro-2'-[N-(ethoxycarbonyl)sulfamoyl]-5'-n-propylbiphenyl-4-yl]methyl]-3-n-propyl-1H-pyrazole-5-carbonitrile;

(52) 3-n-butyl-1-[2-chloro-5-[(cyclopropanecarbonyl)amino]phenyl]-4-[[3-fluoro-2'-[N-(2-fluorobenzoyl)sulfamoyl]-5'-n-propylbiphenyl-4-yl]methyl]-1H-pyrazole-5-carbonitrile;

(53) 3-n-butyl-1-[2-chloro-5-[(cyclopropanecarbonyl)amino]phenyl]-4-[[2'-[N-(ethoxycarbonyl)sulfamoyl]-3-fluoro-5'-n-propylbiphenyl-4-yl]methyl]-1H-pyrazole-5-carbonitrile;

(54) 3-n-butyl-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carboxylic acid;

(55) methyl 3-n-butyl-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carboxylate;

(56) 3-n-butyl-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carboxamide;

(57) 3-n-butyl-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-(N-methylcarboxamide);

(58) 3-n-butyl-4-[[3-fluoro-2'-[N-(2-fluorobenzoyl)sulfamoyl]biphenyl-4-yl]methyl]-1-[5-[(2-methoxyacetyl)amino]-2-((trifluoromethyl)phenyl]-1H-pyrazole-5-(N,N-dimethylcarboxamide);

(59) 3-n-butyl-4-[[2'-[N-(2-chlorobenzoyl)sulfamoyl]-3-fluorobiphenyl-4-yl]methyl]-1-[5-[(2-methoxyacetyl)amino]-2-(trifluoromethyl)phenyl]-1H-pyrazole;

(60) 3-n-butyl-5-chloro-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole;

(61) 3-n-butyl-4-[[3-fluoro-2'-[N-(2-fluorobenzoyl)sulfamoyl]biphenyl-4-yl]methyl]-5-hydroxy-1-[5-(propionylamino)-2-(trifluoromethyl)phenyl]-1H-pyrazole;

(62) 3-n-butyl-4-[[3-fluoro-2'-[N-(2-fluorobenzoyl)sulfamoyl]biphenyl-4-yl]methyl]-5-methoxy-1-[5-[(2-methoxyacetyl)amino]-2-(trifluoromethyl)phenyl]-1H-pyrazole;

(63) 3-n-butyl-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-5-(methylthio)-1H-pyrazole;

(64) 3-n-butyl-1-[5-[(2-ethoxyacetyl)amino]-2-(trifluoromethyl)phenyl]-4-[[3-fluoro-2'-[N-(2-fluorobenzoyl)sulfamoyl]biphenyl-4-yl]methyl]-5-(methanesulfonyl)-1H-pyrazole;

(65) 5-amino-3-n-butyl-4-[[3-fluoro-2'-[N-(2-fluorobenzoyl)sulfamoyl]biphenyl-4-yl]methyl]-1-[5-(propionylamino)-2-(trifluoromethyl)phenyl]-1H-pyrazole;

(66) 3-n-butyl-4-[[3-fluoro-2'-[N-(2-fluorobenzoyl)sulfamoyl]biphenyl-4-yl]methyl]-5-(methylamino)-1-[5-[(2-methoxyacetyl)amino]-2-(trifluoromethyl)phenyl]-1H-pyrazole;

(67) 3-n-butyl-5-(dimethylamino)-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole;

(68) 3-n-butyl-4-[[2'-[N-(3-chloro-2-thiophenecarbonyl)sulfamoyl]-3-fluorobiphenyl-4-yl]methyl]-1-[5-[(2-methoxyacetyl)amino]-2-(trifluoromethyl)phenyl]-1H-pyrazole-5-carbonitrile;

(69) 3-n-butyl-4-[[2'-[N-(3,3-dimethylbutyryl)sulfamoyl]-3-fluorobiphenyl-4-yl]methyl]-1-[5-[(2-methoxyacetyl)amino]-2-(trifluoromethyl)phenyl]-1H-pyrazole-5-carbonitrile;

(70) 3-n-butyl-4-[[2'-[N-(ethoxycarbonyl)sulfamoyl]-3-fluorobiphenyl-4-yl]methyl]-1-[5-[(2-methoxyacetyl)amino]-2-(trifluoromethyl)phenyl]-1H-pyrazole-5-carbonitrile;

(71) 3-n-butyl-4-[[3-fluoro-2'-[N-(isopropoxycarbonyl)sulfamoyl]biphenyl-4-yl]methyl]-1-[5-[(2-methoxyacetyl)amino]-2-(trifluoromethyl)phenyl]-1H-pyrazole-5-carbonitrile;

(72) 3-n-butyl-4-[[3-fluoro-2'-[N-(n-propoxycarbonyl)sulfamoyl]biphenyl-4-yl]methyl]-1-[5-[(2-methoxyacetyl)amino]-2-(trifluoromethyl)phenyl]-1H-pyrazole-5-carbonitrile;

(73) 3-n-butyl-4-[[3,3'-difluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carbonitrile;

(74) 3-n-butyl-1-[5-(N-n-butylcarbamoyl)-2-(trifluoromethyl)phenyl]-4-[[3,3'-difluoro-2'-[N-(2-fluorobenzoyl)sulfamoyl]biphenyl-4-yl]methyl]-1H-pyrazole-5-carbonitrile;

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| Active ingredient | 50 |
| Lactose | 149 |
| Magnesium stearate | 1 |
| Capsule (size No. 1) | 200 |

The active ingredient can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain the active ingredient (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of the active ingredient (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain the active ingredient (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain the active ingredient (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula:

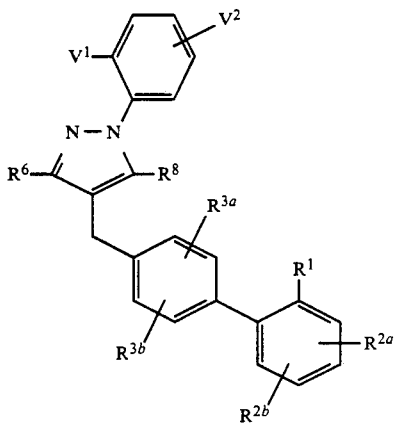

I or a pharmaceutically acceptable salt thereof wherein:
$R^1$ is $-SO_2NHCOR^{23}$ or $-SO_2NHCO_2R^{24}$;
$R^{2a}$ and $R^{2b}$ are independently: H, F, Cl, $CF_3$ or $C_1-C_4$-alkyl;
$R^{3a}$ is H or F;
$R^{3b}$ is H, F, Cl, $CF_3$ or $C_1-C_4$-alkyl;
$R^6$ is $C_1-C_6$-alkyl;
$R^8$ is H, F, Cl, Br, I, $-OH$, $-O(C_1-C_4$-alkyl), $-S(O)_p(C_1-C_4$-alkyl), $-NH_2$, $-NH(C_1-C_4$-alkyl), $-N(C_1-C_4$-alkyl)$_2$, $-CN$, $-CO_2H$, $-CO_2(C_1-C_4$-alkyl), $-CONH_2$, $CONH(C_1-C_4$-alkyl) or $-CON-(C_1-C_4$-alkyl)$_2$;
$V^1$ is $CH_3$, $CF_3$, Cl, Br, I, F, $OCH_3$, $SCH_3$, $-NO_2$ or $-CN$;
$V^2$ is a group at the 4- or 5-position selected from:
 (a) $-NR^{21}COR^{22}$,
 (b) $-NR^{21}CO_2R^{22}$,
 (c) $-NR^{21}CONR^{21}R^{22}$,

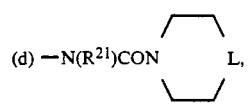

(e) $-CONR^{21}R^{22}$,

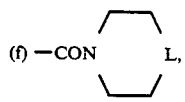

(g) $-COR^{22}$,
 (h) $-S(O)_pR^{22}$,
 (i) $-SO_2NR^{21}R^{22}$,

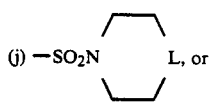

(k) $-NR^{21}SO_2R^{22}$,
wherein L is a single bond, $CH_2$, O, $S(O)_p$, or $NR^9$, and p is 0 to 2;
$R^{21}$ is:
 (a) H or
 (b) straight chain or branched $C_1-C_6$-alkyl, $C_3-C_6$-alkenyl, or $C_3-C_6$-alkynyl, each of which is unsubstituted or substituted with one or more substituents selected from the group consisting of aryl, heteroaryl, $C_3-C_6$-cycloalkyl, Cl, Br, I, F, $-OH$, $-O(C_1-C_4$-alkyl), $-S(C_1-C_4$-alkyl), $-O$—phenyl or $-S$—phenyl;
$R^{22}$ is:
 (a) straight chain or branched $C_1-C_6$-alkyl, $C_2-C_6$-alkenyl, or $C_2-C_6$-alkynyl, each of which is unsubstituted or substituted with one or more substituents selected from the group consisting of aryl, heteroaryl, $C_3-C_6$-cycloalkyl, Cl, Br, I, F, $-OH$, $-O(C_1-C_4$-alkyl), $-S(C_1-C_4$-alkyl), $-O$—phenyl or $-S$—phenyl,
 (b) $C_3-C_7$-cycloalkyl unsubstituted or substituted with one or more substituents selected from the group consisting of $C_1-C_4$-alkyl, Cl, Br, I, F or phenyl,
 (c) aryl, or
 (d) heteroaryl;
$R^{23}$ is:
 (a) aryl,
 (b) heteroaryl,
 (c) straight chain or branched $C_1-C_6$-alkyl, $C_3-C_6$-alkenyl, or $C_3-C_6$-alkynyl, each of which is unsubstituted or substituted with one or more substituents selected from the group consisting of aryl, heteroaryl, $C_3-C_6$-cycloalkyl, Cl, Br, I, F, $-OH$, $-O(C_1-C_4$-alkyl), $-S(C_1-C_4$-alkyl), $-O$—phenyl or $-S$—phenyl,
 (d) $C_3-C_7$-cycloalkyl unsubstituted or substituted with one or more substituents selected from the group consisting of $C_1-C_4$-alkyl, Cl, Br, I, F, or phenyl,
 (e) $C_7-C_{10}$-bi- or tricycloalkyl, or
 (f) saturated 5- or 6-membered heterocyclyl linked through a carbon atom and containing one or two heteroatoms selected from oxygen or sulfur;
$R^{24}$ is:
 (a) straight chain or branched $C_1-C_6$-alkyl, $C_3-C_6$-alkenyl, or $C_3-C_6$-alkynyl, each of which is unsubstituted or substituted with one or more substituents selected from the group consisting of aryl, $C_3-C_6$-cycloalkyl, Cl, Br, I, F, $-O(C_1-C_4$-alkyl), $-S(C_1-C_4$-alkyl), $-O$—phenyl or $-S$—phenyl, (b) $C_3$-$C_7$-cycloalkyl unsubstituted or substituted with one or more substituents selected from the group consisting of $C_1$-$C_4$-alkyl, Cl, Br, I, F or phenyl, or (c) aryl.

2. The compound of claim 1 or a pharmaceutically acceptable salt thereof wherein:

$R^{2a}$ is H or F;
$R^{2b}$ is H, F or $C_1$-$C_4$-alkyl;
$R^{3b}$ is H, F or Cl;
$R^6$ is n-propyl or n-butyl;
$R^8$ is —CN, —$CO_2H$, —$CO_2(C_1$-$C_4$-alkyl), —$CONH_2$, —$CONH(C_1$-$C_4$-alkyl) or —$CON(C_1$-$C_4$-alkyl)_2$;
$R^{21}$ is H;
$R^{23}$ is:

(a) phenyl, unsubstituted or substituted with one or two substituents chosen from Cl, Br, F, I, methyl or trifluoromethyl, at least one of which occupies an ortho-position;

(b) heteroaryl, selected from furan-2-yl, thiophen-2-yl, benzo[b]furan-2-yl, benzo[b]thiophen-2-yl, furan-3-yl, thiophen-3-yl, and oxazol-5-yl, unsubstituted or substituted with one or two substituents chosen from Cl, Br, F, I, methyl or trifluoromethyl, wherein at least one of the substituents is located adjacent to the carbonyl substituent and/or to a ring heteroatom;

(c) branched $C_3$-$C_6$-alkyl;

(d) $C_3$-$C_7$-cycloalkyl, unsubstituted or substituted at the 1-and/or 2-position with one or two substituents chosen from Cl, Br, F, I, methyl or ethyl;

(e) $C_7$-$C_{10}$-bi- or tricycloalkyl; or (f) saturated 5- or 6-membered heterocyclyl linked through a carbon atom and containing one or two heteroatoms selected from oxygen and sulfur;

$R^{24}$ is straight chain or branched $C_1$-$C_6$-alkyl, $C_3$-$C_6$-alkenyl, or $C_3$-$C_6$-alkynyl, each of which is unsubstituted or substituted with aryl or $C_3$-$C_6$-cycloalkyl;

$V^1$ is $CF_3$, Cl, Br, I, or F;

$V^2$ is a group at the 5-position selected from:

(a) —$NR^{21}COR^{22}$;
(b) —$NR^{21}CO_2R^{22}$;
(c) —$NR^{21}CONR^{21}R^{22}$;

(d) 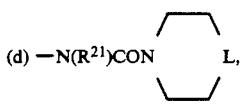

(e) —$CONR^{21}R^{22}$;

(f) 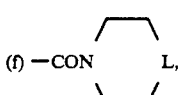

(g) —$COR^{22}$; or
(h) —$S(O)_pR^{22}$.

3. The compound of claim 2 which is:

(1) 3-n-butyl-4-[[2'-[N-(2-chlorobenzoyl)sulfamoyl]-3-fluorobiphenyl-4-yl]methyl]-1-[2-chloro-5-(propionylamino)phenyl]-1H-pyrazole-5-carbonitrile;

(2) 3-n-butyl-4-[[2'-[N-(2-chlorobenzoyl)sulfamoyl]-3-fluorobiphenyl-4-yl]methyl]-1-[2-chloro-5-(valerylamino)phenyl]-1H-pyrazole-5-carbonitrile;

(3) 3-n-butyl-4-[[2'-[N-(2-chlorobenzoyl)sulfamoyl]-3-fluorobiphenyl-4-yl]methyl]-1-[5-(propionylamino)-2-(trifluoromethyl)phenyl]-1H-pyrazole-5-carbonitrile;

(4) 3-n-butyl-4-[[2'-[N-(2-chlorobenzoyl)sulfamoyl]-3-fluorobiphenyl-4-yl]methyl]-1-[5-[(2-methoxyacetyl)amino]-2-(trifluoromethyl)phenyl]-1H-pyrazole-5-carbonitrile;

(5) 3-n-butyl-4-[[2'-[N-(2-chlorobenzoyl)sulfamoyl]-3-fluorobiphenyl-4-yl]methyl]-1-[2-chloro-5-[(2-ethoxyacetyl)amino]phenyl]-1H-pyrazole-5-carbonitrile;

(6) 3-n-butyl-4-[[3-fluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carbonitrile;

(7) 3-n-butyl-4-[[3-fluoro-2'-[N-(2-fluorobenzoyl)sulfamoyl]biphenyl-4-yl]methyl]-1-[5-[(2-ethoxyacetyl)amino]-2-(trifluoromethyl)phenyl]-1H-pyrazole-5-carbonitrile;

(8) 3-n-butyl-1-[5-(N-n-butylcarbamoyl)-2-(trifluoromethyl)phenyl]-4-[[2'-[N-(2-chlorobenzoyl)sulfamoyl]-3-fluorobiphenyl-4-yl]methyl]-1H-pyrazole-5-carbonitrile;

(9) 3-n-butyl-1-[5-(N-n-butylcarbamoyl)-2-(trifluoromethyl)phenyl]-4-[[3-fluoro-2'-[N-(2-fluorobenzoyl)sulfamoyl]biphenyl-4-yl]methyl]-1H-pyrazole-5-carbonitrile;

(10) 4-[[3-fluoro-2'-[N-(2-fluorobenzoyl)sulfamoyl]biphenyl-4-yl]methyl]-1-[5-[(methoxyacetyl)amino]-2-(trifluoromethyl)phenyl]-3-n-propyl-1H-pyrazole-5-carbonitrile;

(11) 1-[5-[(ethoxyacetyl)amino]-2-(trifluoromethyl)phenyl]-4-[[3-fluoro-2'-[N-(2-fluorobenzoyl)sulfamoyl]biphenyl-4-yl]methyl]-3-n-propyl-1H-pyrazole-5-carbonitrile;

(12) 1-[5-(N-n-butylcarbamoyl)-2-chlorophenyl]-4-[[2'-[N-(2-chlorobenzoyl)sulfamoyl]-3-fluorobiphenyl-4-yl]methyl]-3-n-propyl-1H-pyrazole-5-carbonitrile;

(13) 1-[5-(N-n-butylcarbamoyl)-2-chlorophenyl]-4-[[3-fluoro-2'-[N-(2-fluorobenzoyl)sulfamoyl]biphenyl-4-yl]methyl]-3-n-propyl-1H-pyrazole-5-carbonitrile;

(14) 1-[5-(N-n-butylcarbamoyl)-2-(trifluoromethyl)phenyl]-4-[[2'-[N-(2-chlorobenzoyl)sulfamoyl]-3-fluorobiphenyl-4-yl]methyl]-3-n-propyl-1H-pyrazole-5-carbonitrile;

(15) 1-[5-(N-n-butylcarbamoyl)-2-(trifluoromethyl)phenyl]-4-[[3-fluoro-2'-[N-(2-fluorobenzoyl)sulfamoyl]biphenyl-4-yl]methyl]-3-n-propyl-1H-pyrazole-5-carbonitrile;

(16) 1-[5-(acetylamino)-2-chlorophenyl]-3-n-butyl-4-[[3-fluoro-2'-[N-(2-fluorobenzoyl)sulfamoyl]-5'-n-propylbiphenyl-4-yl]methyl]-1H-pyrazole-5-carbonitrile; or

(17) 1-[5-(acetylamino)-2-chlorophenyl]-3-n-butyl-4-[[3-fluoro-2'-[N-(ethoxycarbonyl)sulfamoyl]-5'-n-propylbiphenyl-4-yl]methyl]-1H-pyrazole-5-carbonitrile;

(18) 3-n-butyl-4-[[3,3'-difluoro-2'-[N-(2-fluorobenzoyl)sulfamoyl]biphenyl-4-yl]methyl]-1-[5-[(2-methoxyacetyl)amino]-2-(trifluoromethyl)phenyl]-1H-pyrazole-5-carbonitrile.

4. A pharmaceutical formulation for the treatment of hypertension and/or congestive heart failure comprising a pharmaceutical carrier and an effective amount of a compound of claim 1.

5. A pharmaceutical formulation for the treatment of hypertension and/or congestive heart failure comprising a pharmaceutical carrier and an effective amount of a compound of claim 2.

6. A pharmaceutical formulation for the treatment of hypertension and/or congestive heart failure comprising a pharmaceutical carrier and an effective amount of a compound of claim 3.

7. A method of treatment of hypertension and/or congestive heart failure comprising the administration to a patient in need of such treatment of an effective amount of the compound of claim 1.

* * * * *